United States Patent
Kennard et al.

(10) Patent No.: US 10,945,926 B2
(45) Date of Patent: Mar. 16, 2021

(54) LOCKING ENTERAL FEEDING SYSTEM

(71) Applicants: Claborn Kennard, Oklahoma City, OK (US); Augusta Kennard, Oklahoma City, OK (US)

(72) Inventors: Claborn Kennard, Oklahoma City, OK (US); Augusta Kennard, Oklahoma City, OK (US)

(*) Notice: Subject to any disclaimer, the term of this patent is extended or adjusted under 35 U.S.C. 154(b) by 36 days.

(21) Appl. No.: 15/962,785

(22) Filed: Apr. 25, 2018

(65) Prior Publication Data

US 2018/0303720 A1 Oct. 25, 2018

Related U.S. Application Data

(60) Provisional application No. 62/489,598, filed on Apr. 25, 2017, provisional application No. 62/580,576, filed on Nov. 2, 2017.

(51) Int. Cl.
*A61J 15/00* (2006.01)
*A61M 39/10* (2006.01)
*A61J 1/20* (2006.01)

(52) U.S. Cl.
CPC ....... *A61J 15/0026* (2013.01); *A61J 15/0003* (2013.01); *A61J 15/0011* (2013.01); *A61M 39/1011* (2013.01); *A61J 1/20* (2013.01); *A61M 2039/1094* (2013.01); *A61M 2202/0482* (2013.01)

(58) Field of Classification Search
CPC ............ A61J 15/0026; A61J 15/0011; A61J 15/0003; A61M 39/1011; A61M 2039/1094; A61M 2202/0482
See application file for complete search history.

(56) References Cited

U.S. PATENT DOCUMENTS

| | | | |
|---|---|---|---|
| 2006/0047251 A1* | 3/2006 | Bickford Smith | A61M 39/10 604/240 |
| 2008/0140020 A1* | 6/2008 | Shirley | A61M 39/10 604/240 |
| 2015/0032089 A1* | 1/2015 | Way | A61M 39/1011 604/535 |

OTHER PUBLICATIONS

American National Standard guidance document for ANSI/AAMI ID54:1996/(R)2005, Enteral feeding set connectors and adapters, Association for the Advancement of Medical Instrumentation, established 1996; also available at ansi.org (Year: 1996).*

* cited by examiner

*Primary Examiner* — Bradley J Osinski

(57) ABSTRACT

A fluid delivery device and system is operable to fluidly couple a pair of fluid delivery conduits. One embodiment includes a fluid delivery device sized to meet ANSI/AAMI ID54:1996(R) 2005 and not mate with ANSI/HIMA MD70.1 or ISO 594/1 and ISO 594/2 standards for intravenous ports and connectors to prevent accidental intravenous delivery of fluids intended for enteral delivery. The system includes at least one of a locking tab and a stop flange configured to not mate with matching connectors not configured to satisfy the enteral feeding standards and not specifically configured to mate with the fluid delivery device.

14 Claims, 20 Drawing Sheets

Fluid delivery system
10

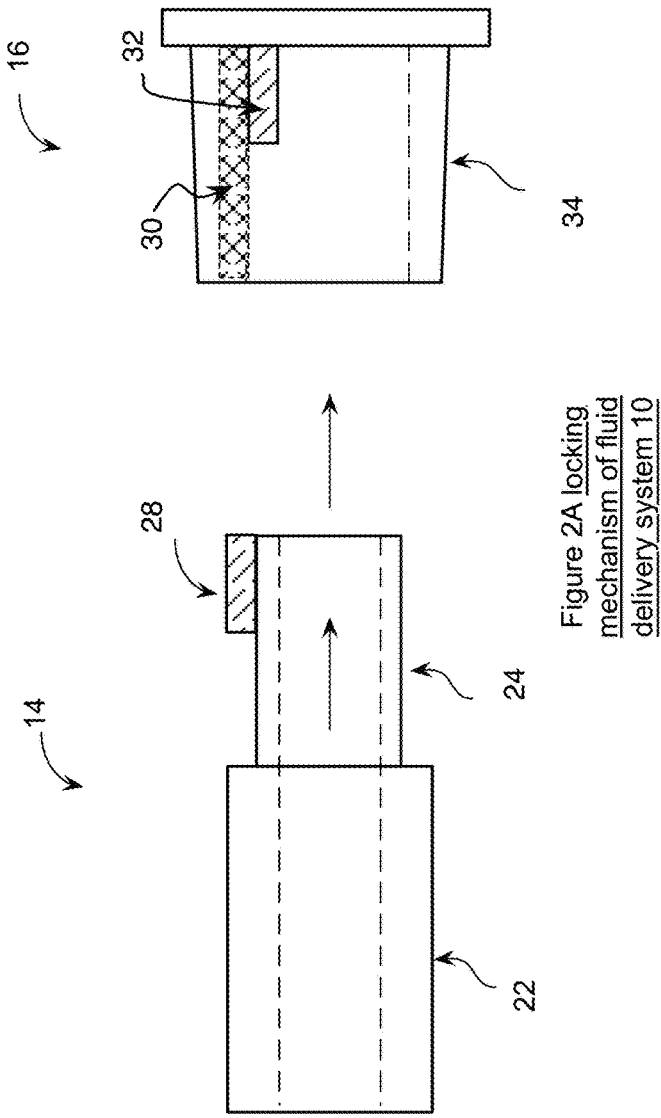
Figure 2A locking mechanism of fluid delivery system 10
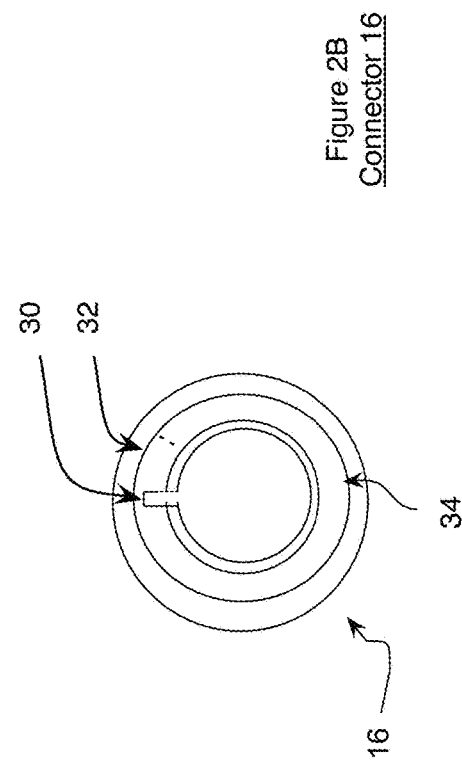
Figure 2B Connector 16

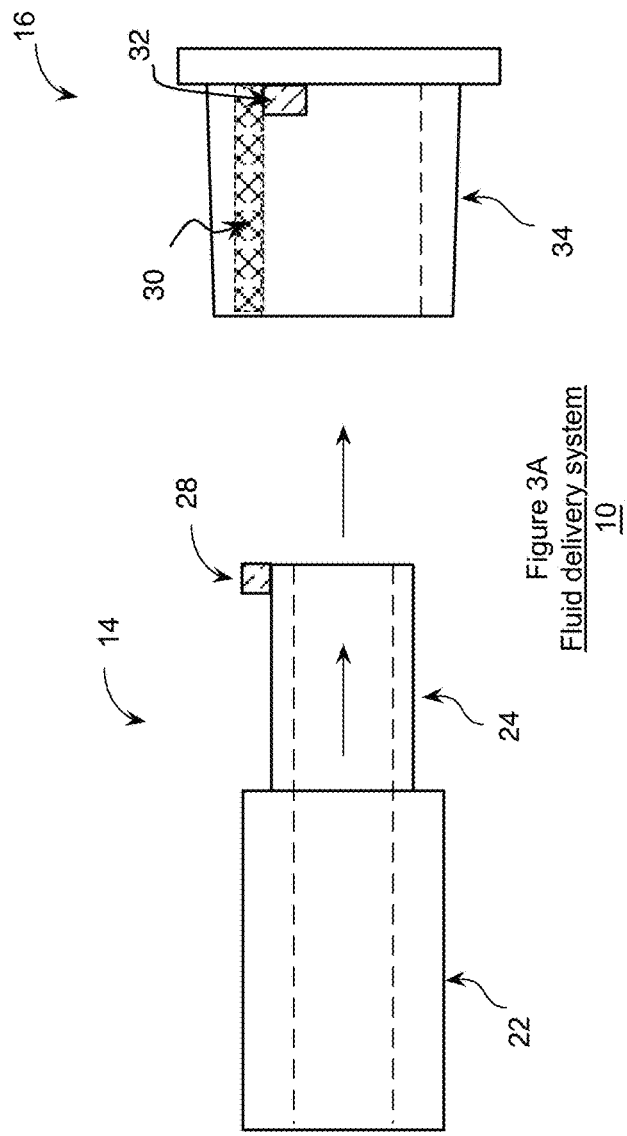
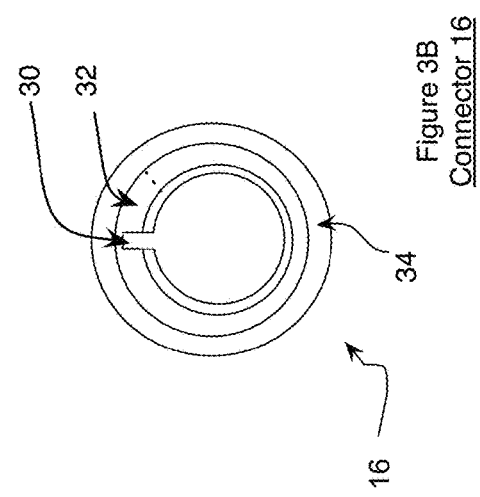
Figure 3A
Fluid delivery system
10
Figure 3B
Connector 16

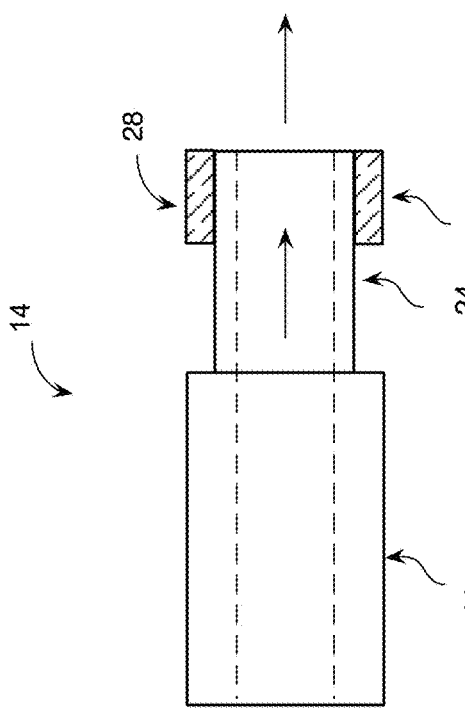
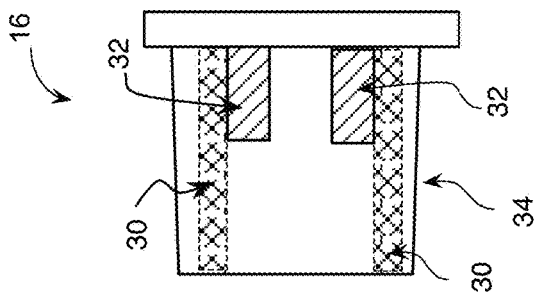
Figure 4A
Fluid delivery system
50
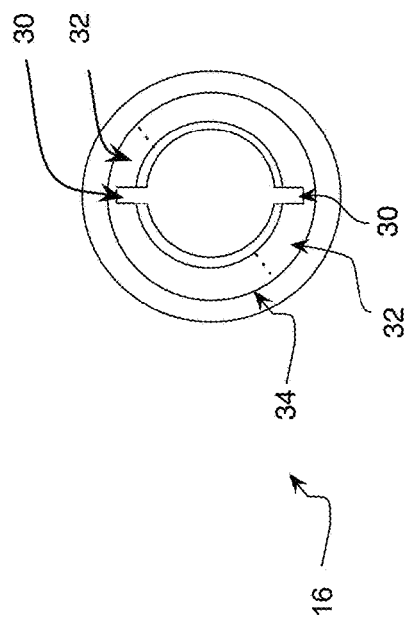
Figure 4B
Connector 16

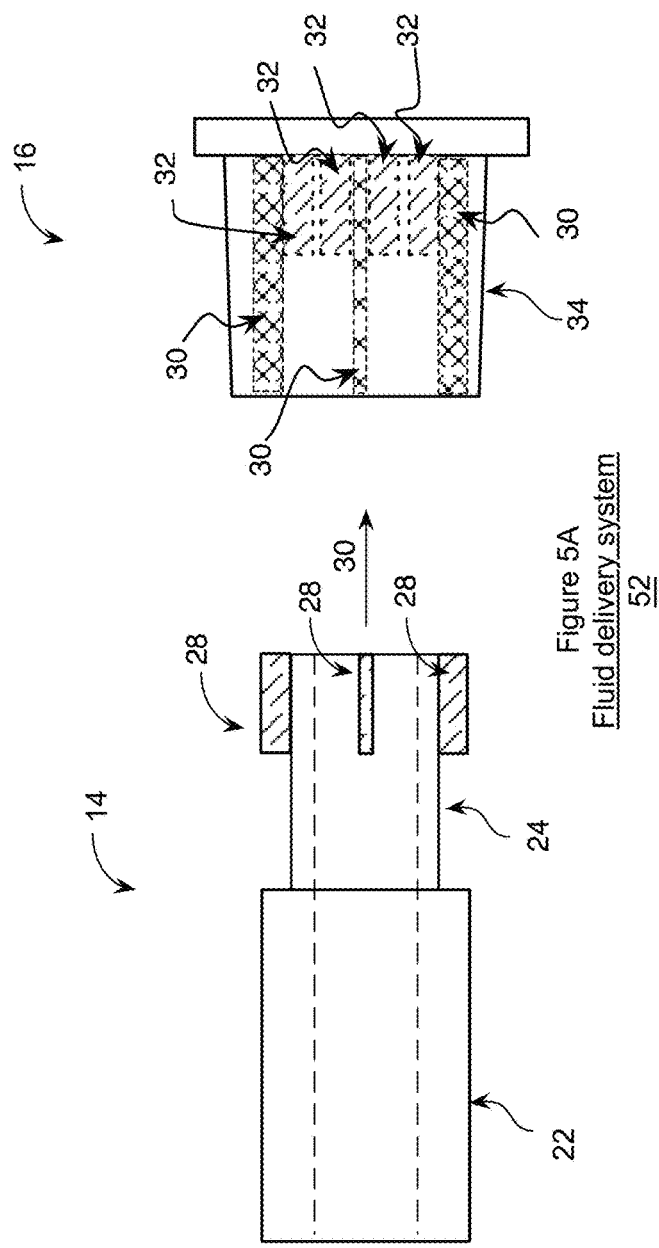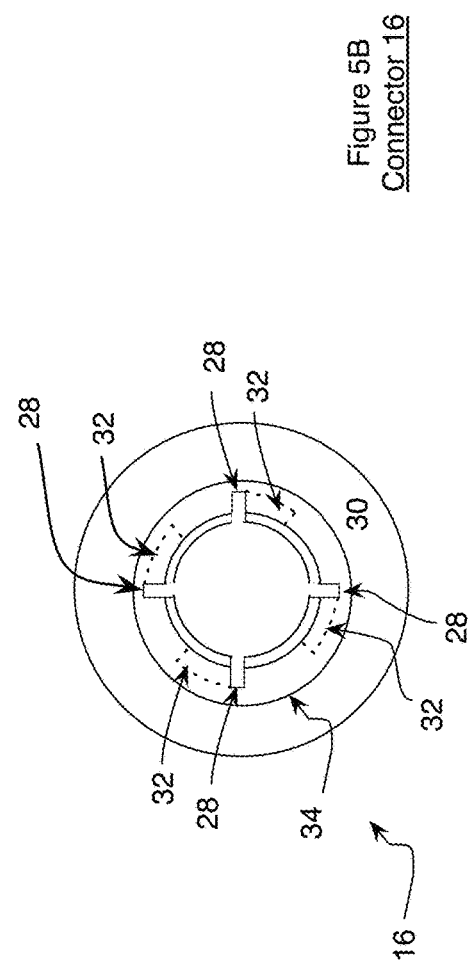

Fluid delivery system 54

Connector 16

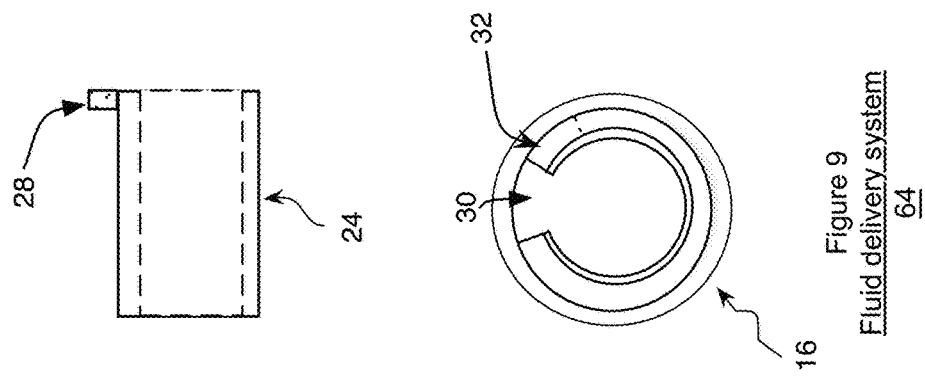
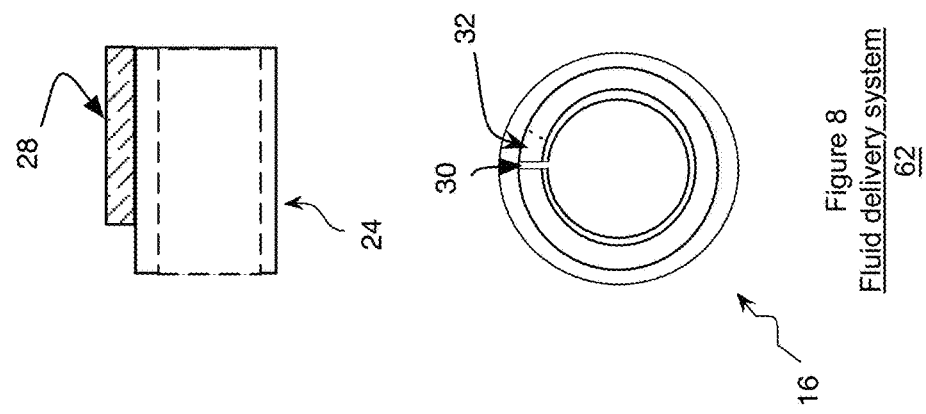
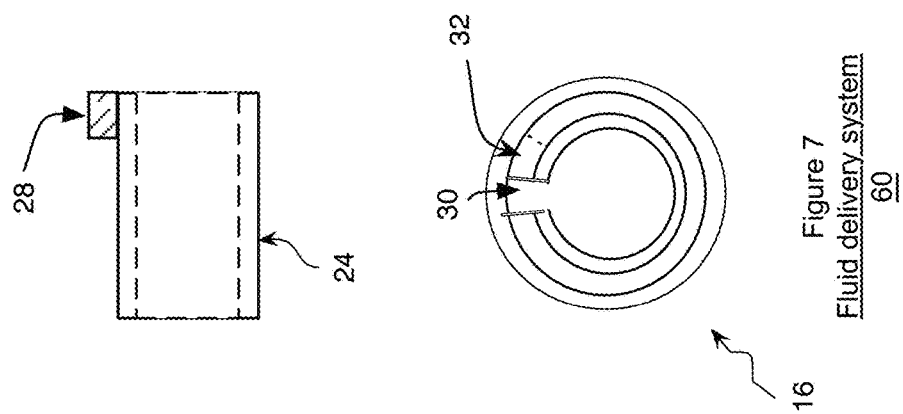

Fluid delivery system
70

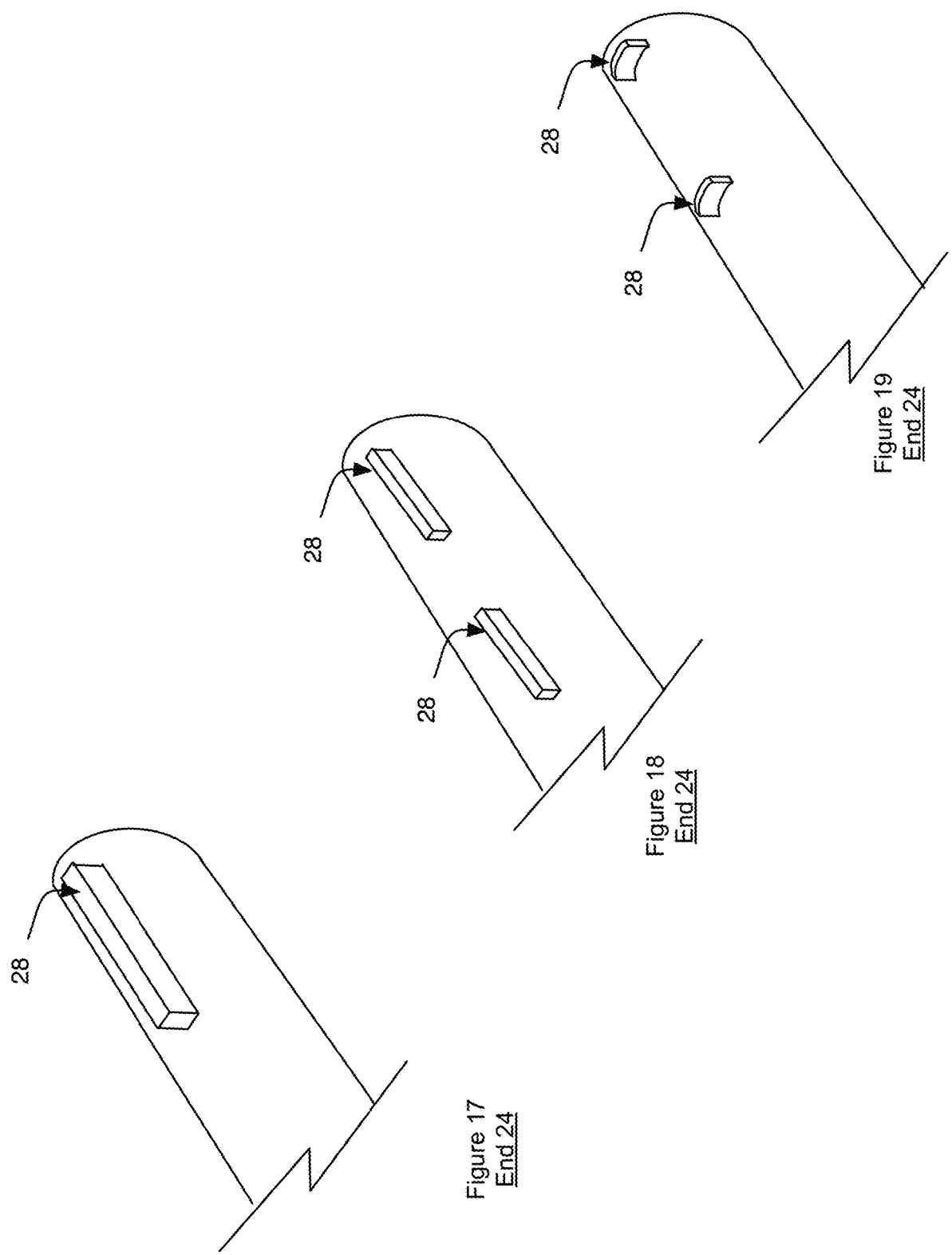

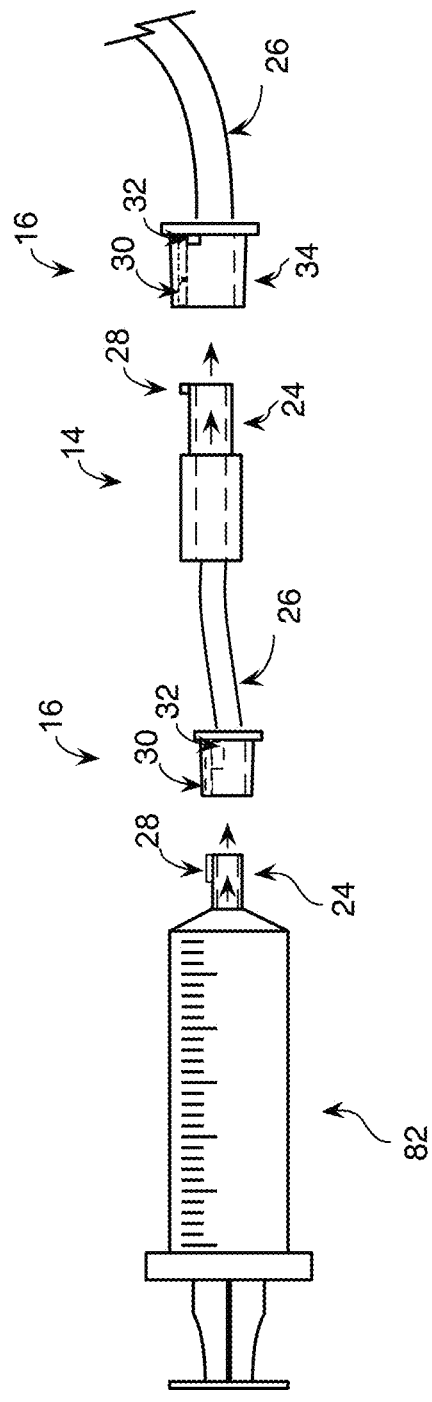
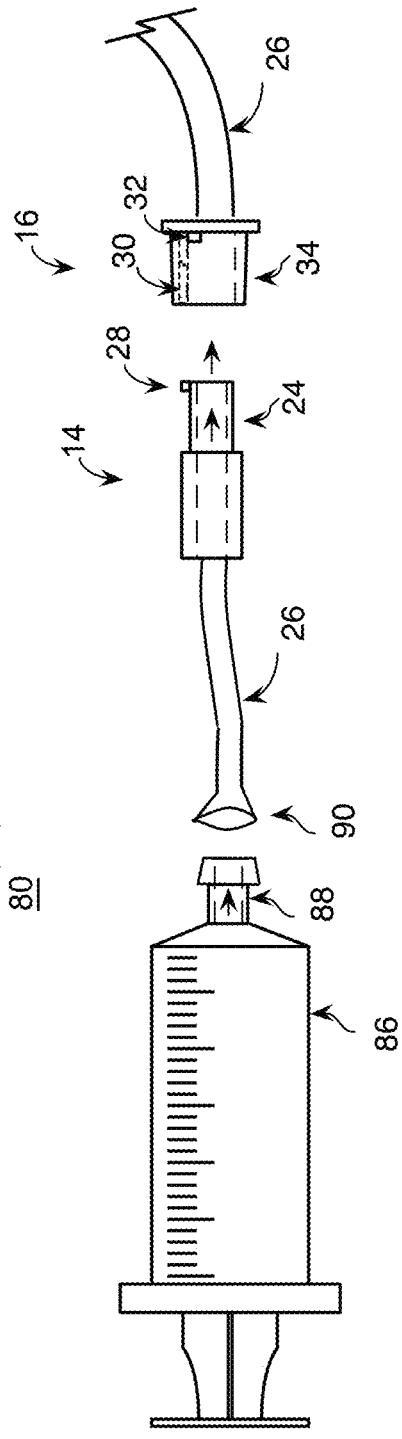
Figure 20
Fluid delivery system
80
Figure 21
Fluid delivery system
84

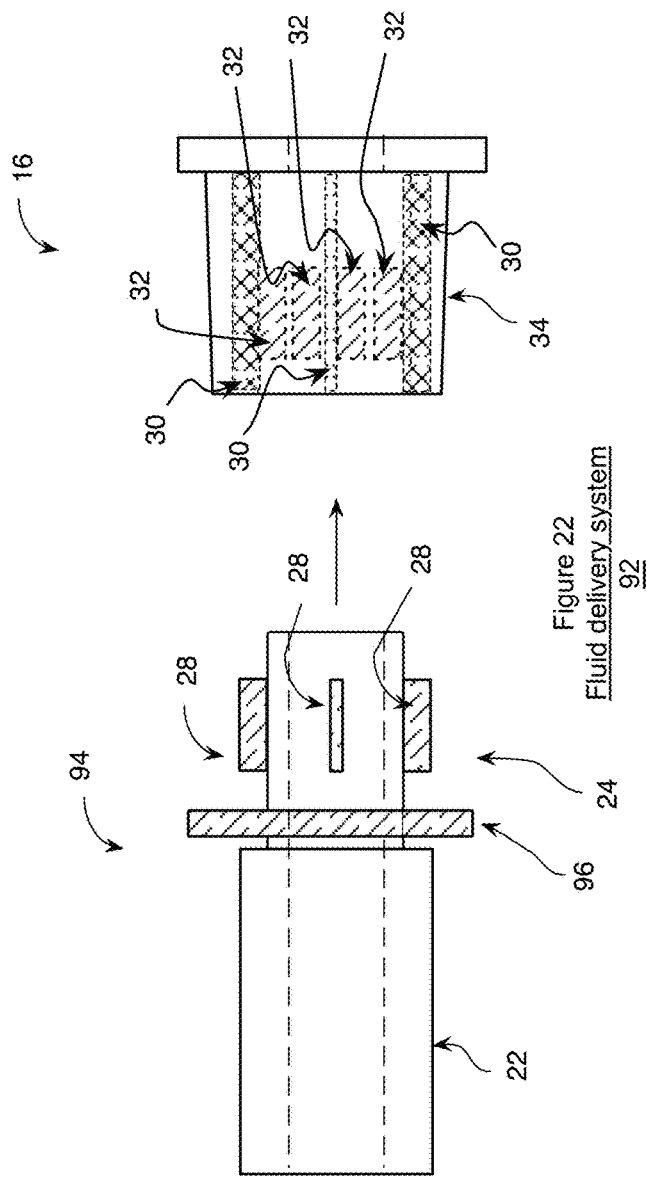
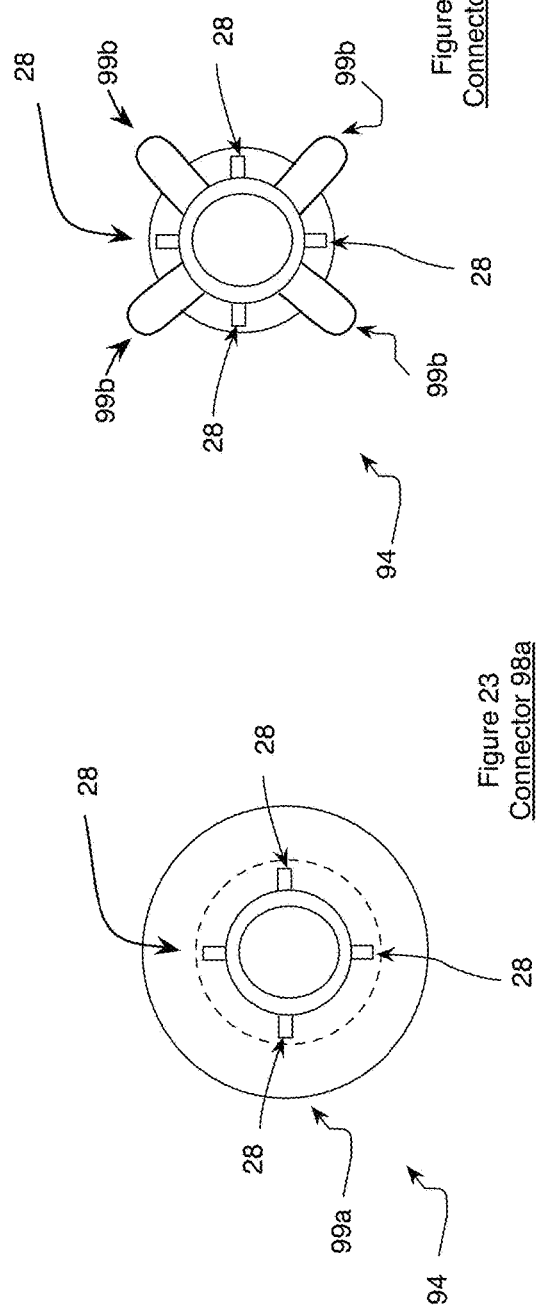

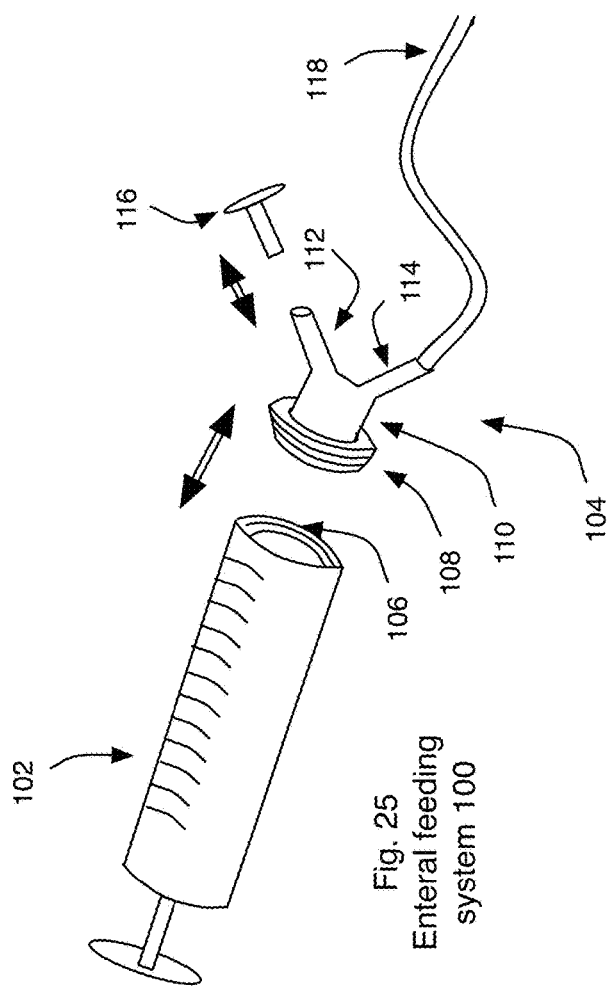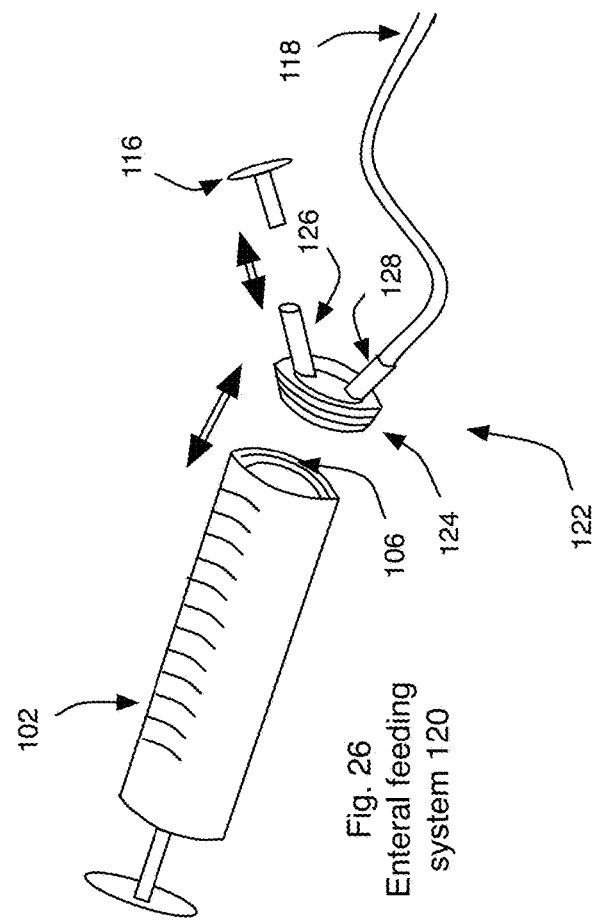

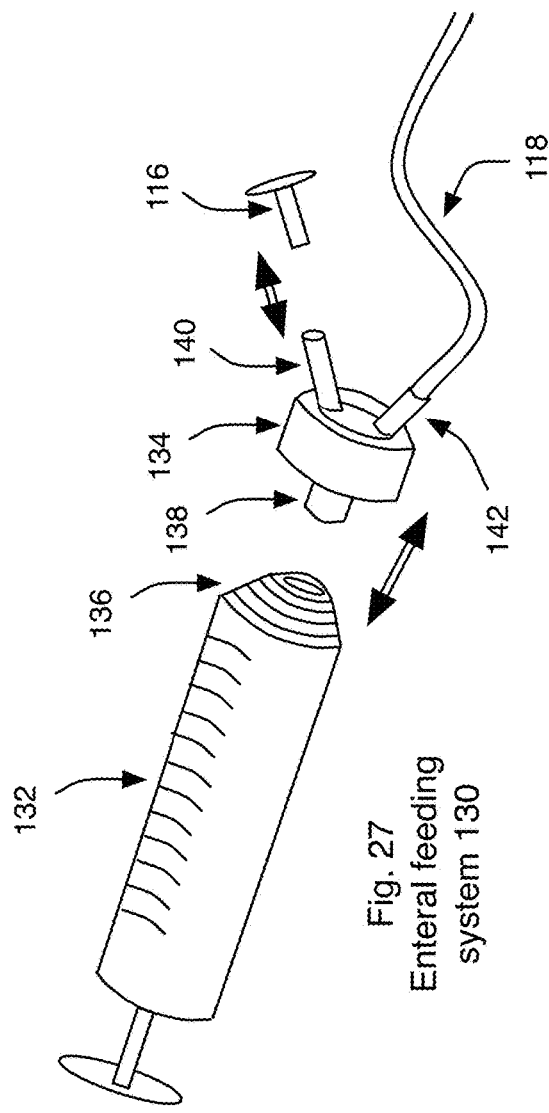
Fig. 27 Enteral feeding system 130
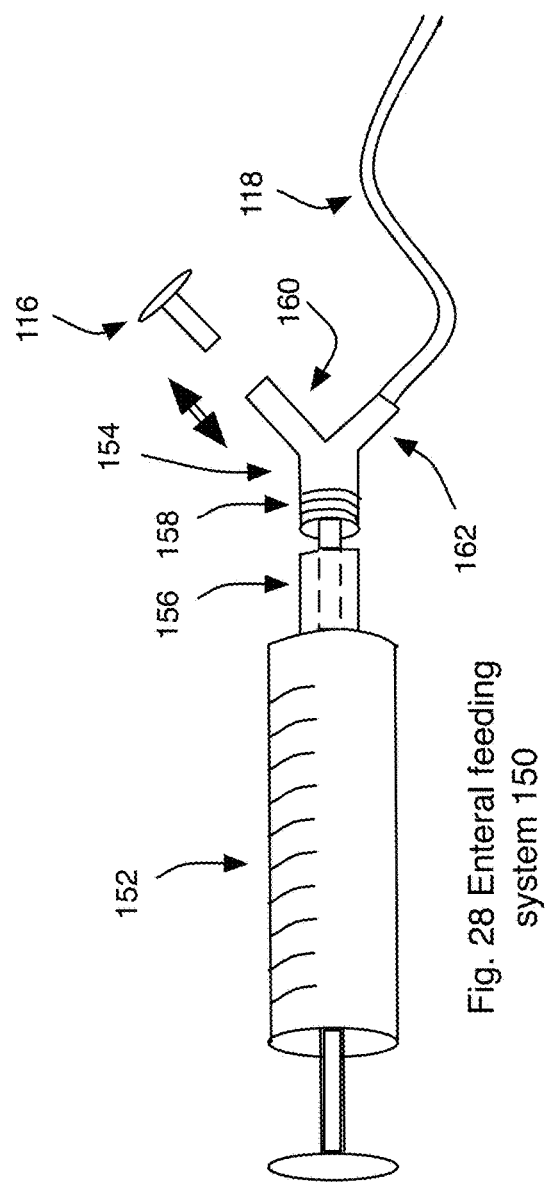
Fig. 28 Enteral feeding system 150

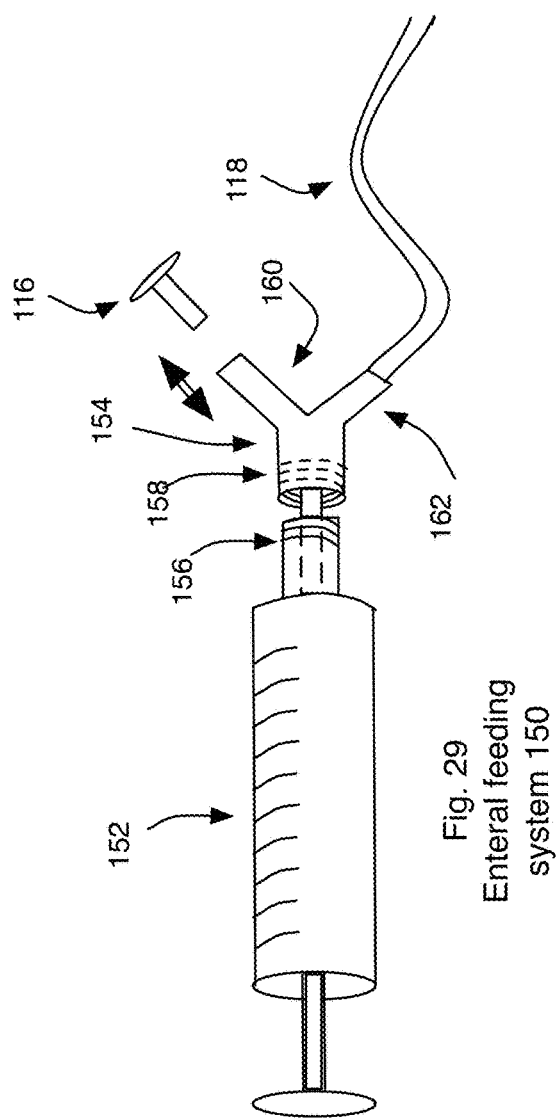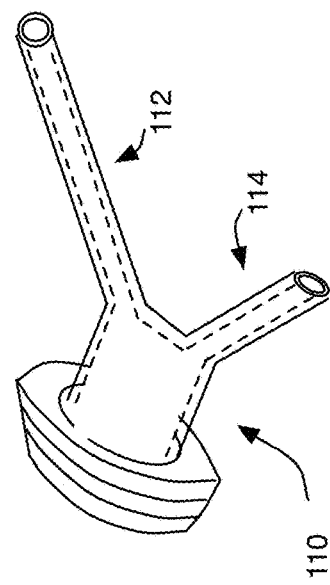

Method 300 for enteral adaptor system

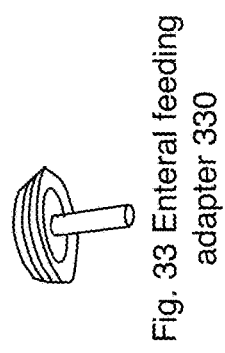
Fig. 33 Enteral feeding adapter 330
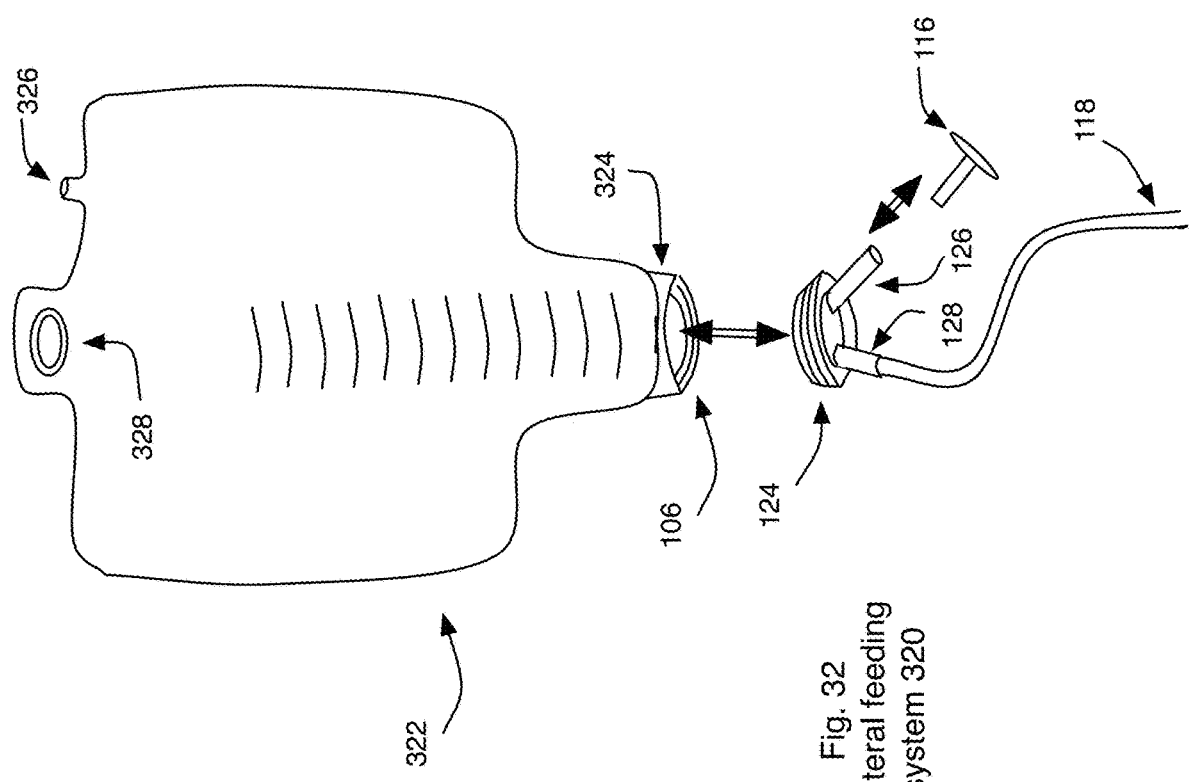
Fig. 32
Enteral feeding system 320

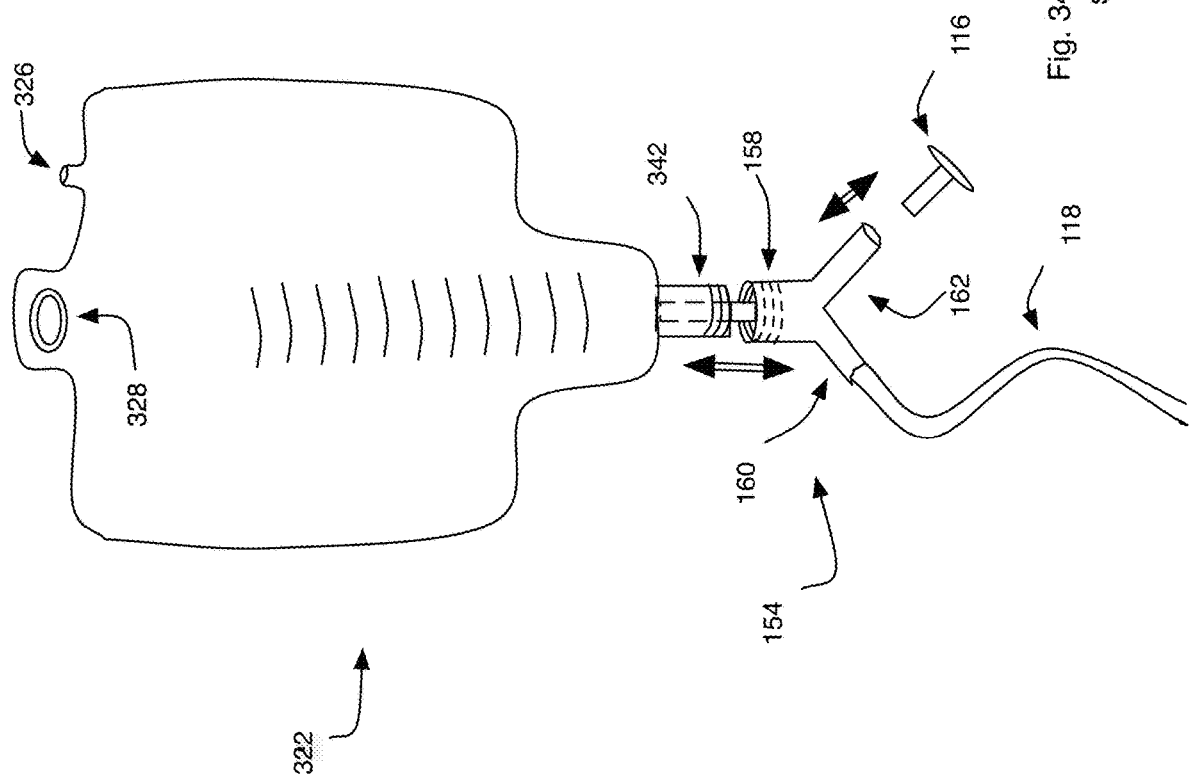

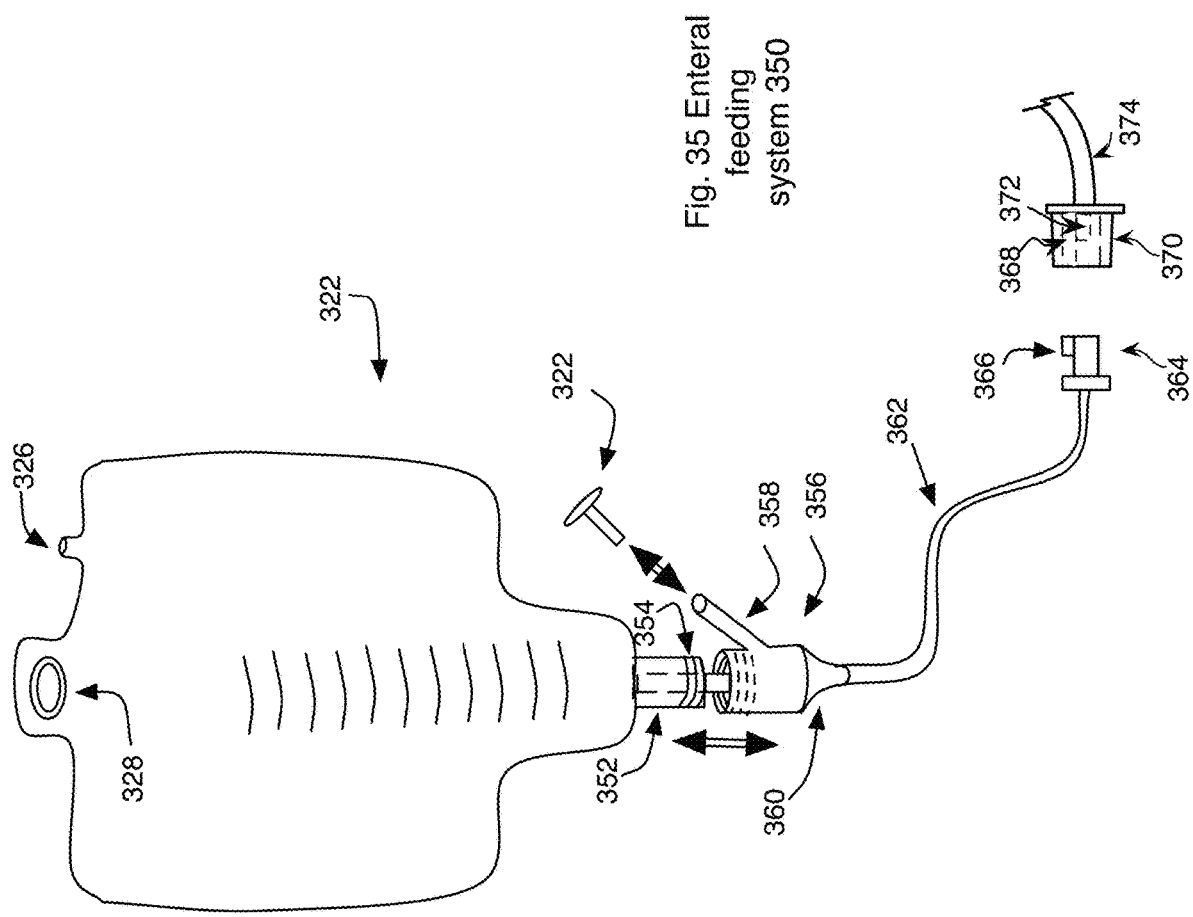

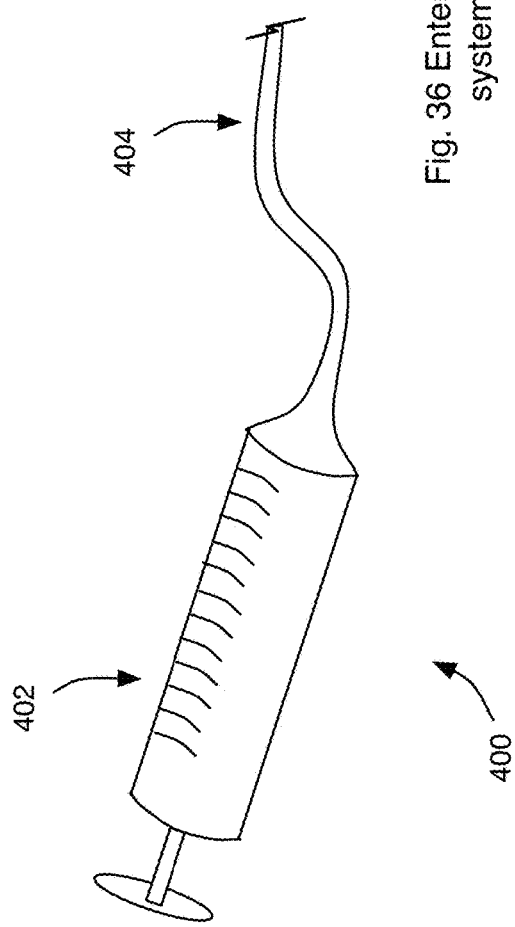
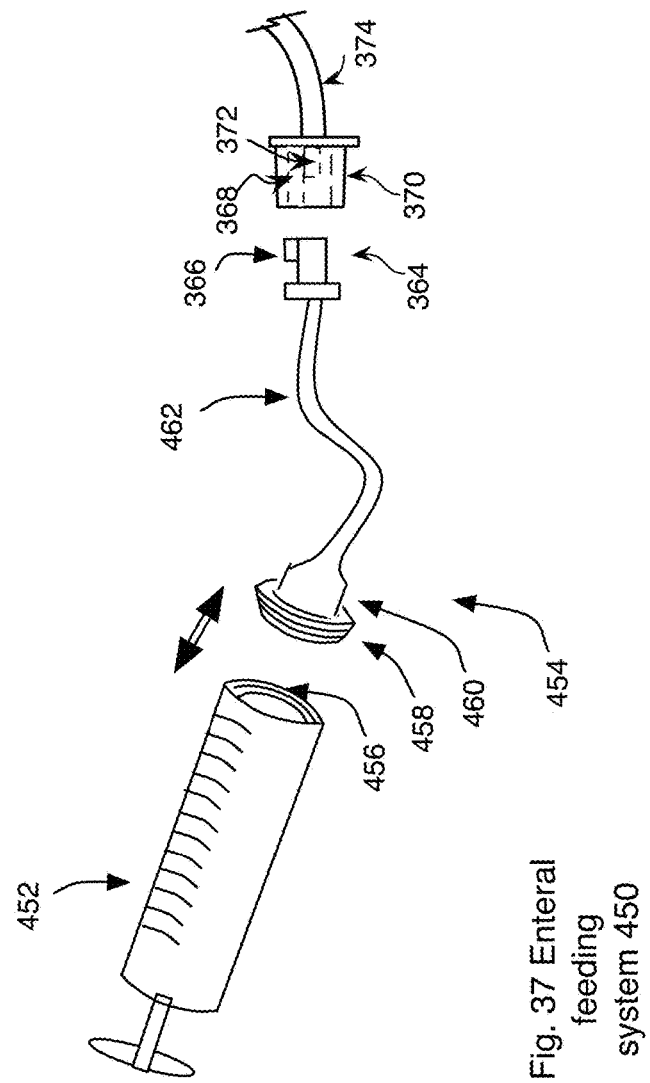

LOCKING ENTERAL FEEDING SYSTEM

CROSS REFERENCE TO RELATED APPLICATIONS

The present U.S. Utility Patent Application claims priority pursuant to 35 U.S.C. § 119(e) to U.S. Provisional Application No. 62/489,598, entitled "SYRINGE OR POUCH ENTERAL FEEDING SYSTEM", filed Apr. 25, 2017, and to U.S. Provisional Application No. 62/580,576, entitled "FLUID DELIVERY DEVICE WITH LOCKING STRUCTURE", filed Nov. 2, 2017, both of which are hereby incorporated herein by reference in their entirety and made part of the present U.S. Utility Patent Application for all purposes.

BACKGROUND

1. Technical Field

The present invention relates to enteral feeding devices and, more particularly, to syringes for enteral feeding that may be connected directly to a feeding tube.

2. Related Art

The present embodiments of the invention relate to medical devices and, more particularly, to connectors for intravenous and enteral delivery of medicinal and nutritional flows that include a structure to prevent misconnections. Fluid delivery systems are known to fill a great necessity for delivery of medicine and nutrients to ill and disabled patients in many settings especially hospitals and health care facilities. For example, in neo-natal units, infants are often fed enterally (e.g., a tube inserted in the mouth or nasal opening (nare) and through the trachea for delivery of the fluid to the stomach or intestinal region of the body) and are also provided medication and other fluids intravenously.

One particular problem includes interfacing differing devices to enable said devices to mechanically couple to deliver a food, sustenance or medicine. For example, formula and breast milk are often delivered by syringe into an enteral delivery system for delivery to the infant's stomach. Tragically, however, through too common of oversight, infants are accidentally killed when a syringe with nutritional food is coupled to an I.V. port and injected into the blood stream. Milk delivered to the heart, however, is usually fatal to the infant.

One reason for such mistakes relates to the technology for delivering food and medicine. Too often, syringes that are used for either delivering food to an enteral delivery system may also be used for delivery of medicine or fluid to an I.V. system. Because these syringes are technically compatible with either system, tragic mistakes are possible and may even be expected.

Thus, a need exists for a device that is compatible with common delivery systems to allow such systems to fluidly communicate. A further need exists for fluid communication devices that are operable to provide safeguards to avoid tragic mistakes.

BRIEF SUMMARY OF THE INVENTION

The present invention is directed to apparatus and methods of operation that are further described in the following Brief Description of the Drawings, the Detailed Description of the Invention, and the claims. Other features and advantages of the present invention will become apparent from the following detailed description of the invention made with reference to the accompanying drawings. While the present disclosure is largely directed to enteral feedings systems, it should be understood that the mechanism illustrated within the disclosure may be used for delivery of any fluid to a patient.

BRIEF DESCRIPTION OF THE DRAWINGS

A better understanding of the present invention can be obtained when the following detailed description of the preferred embodiment is considered with the following drawings, in which:

FIGS. 2A and 2B illustrate additional details of a locking mechanism of fluid delivery system 10 formed according to one embodiment of the invention.

FIGS. 3A and 3B illustrate additional details of a fluid delivery system 10 formed according to one embodiment of the invention.

FIGS. 4A and 4B illustrate additional details of a fluid delivery system 50 formed according to one embodiment of the invention.

FIGS. 5A and 5B illustrate additional details of a fluid delivery system 52 formed according to one embodiment of the invention.

FIGS. 7-9 illustrate example alternatives to shapes of the locking tabs of fluid device deliver ends and corresponding channels of device that receives the locking tabs 28.

FIGS. 17-19 are perspective views of ends 24 of fluid delivery devices with alternative embodiments of locking tabs 28.

FIG. 20 is an alternative embodiment of the invention of a syringe with an integral locking tab for coupling to a connector in a fluid delivery system.

FIG. 21 is an alternative embodiment of an enteral feeding system that includes a syringe that includes a barbed connector configured to receive a tube having an overmolded end.

FIGS. 22, 23 and 24 illustrate an alternative embodiment of the invention a connector with at least one stop flange.

FIG. 25 is an enteral feeding system 100 that includes a syringe and a syringe adaptor according to one embodiment of the invention.

FIG. 26 is an enteral feeding system 120 that includes a syringe and a syringe adaptor according to one embodiment of the invention.

FIG. 27 is an enteral feeding system 130 that includes a syringe and a syringe adaptor according to one embodiment of the invention.

FIG. 28 is an enteral feeding system 130 that includes a syringe and a syringe adaptor according to one embodiment of the invention.

FIG. 29 is an enteral feeding system 130 that includes a syringe and a syringe adaptor according to one embodiment of the invention.

FIG. 30 is an embodiment of an adapter for enteral feeding according to one embodiment of the invention.

FIG. 32 is an embodiment of an enteral feeding system that includes a feeding pouch and adaptor.

FIG. 33 illustrates an alternative embodiment of the invention of an adaptor. As may be seen, enteral feeding adaptor 330 includes only one port 126 or 128.

FIG. 34 is an embodiment of an enteral feeding system that includes a feeding pouch and adaptor.

FIG. 35 is an enteral feeding system with a pouch, an adapter and an enteral connector according to one embodiment of the invention.

FIG. 36 is an enteral feeding system 400 that includes a syringe with a contiguously formed feeding tube according to one embodiment of the invention.

FIG. 37 is an enteral feeding system 450 that includes a syringe and a syringe adaptor according to one embodiment of the invention.

DETAILED DESCRIPTION OF THE DRAWINGS

Figure 1:
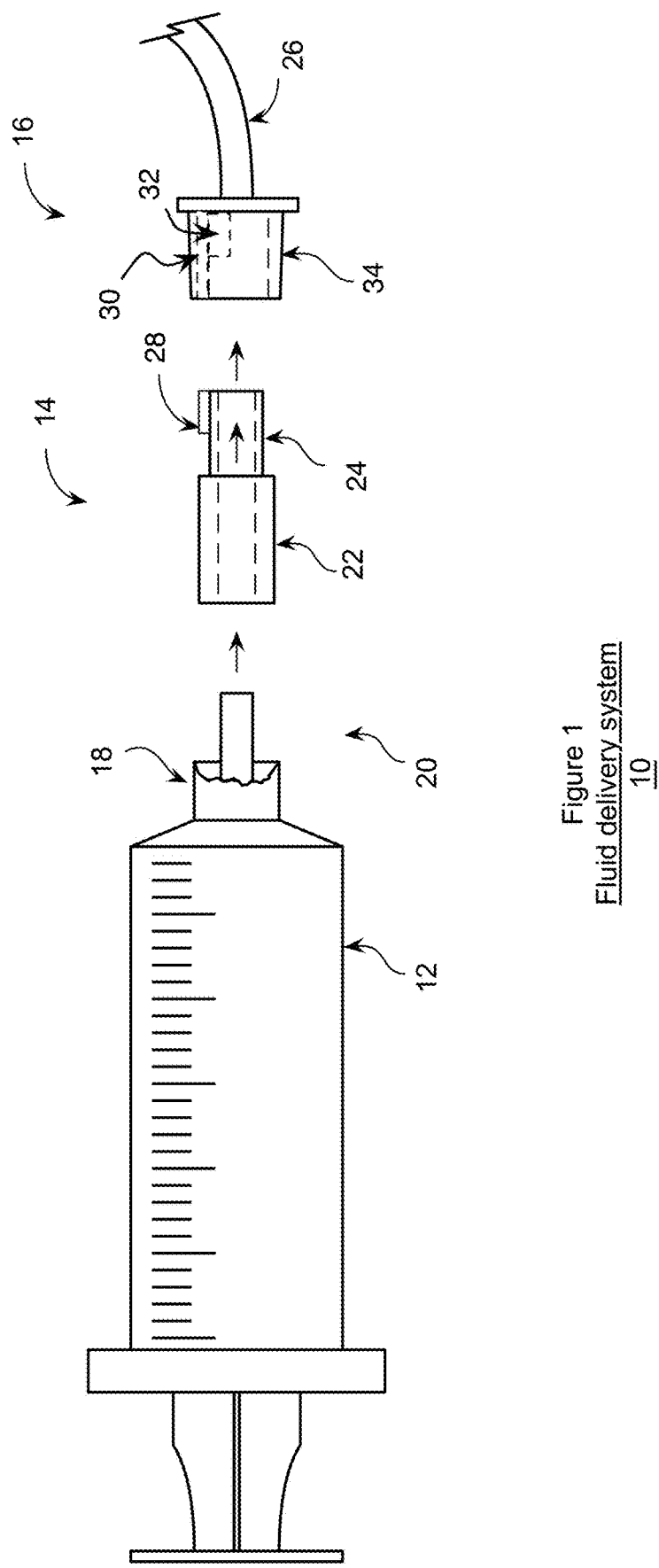
FIG. 1 illustrates an enteral feeding system according to one embodiment that includes a locking structure for locking interconnecting members.

FIG. 1 illustrates an enteral feeding system according to one embodiment that includes a locking structure for locking interconnecting members. Generally, a fluid delivery system 10 includes a fluid delivery device, a matching connector, associated tubing and a syringe. The system 10, more specifically, includes a syringe 12 that is for delivery of medicine intravenously. Additionally, system 10 includes a fluid delivery device 14 that forms an interface between syringe 12 and connector 16. Fluid delivery device 14 is made to permanently adhere to syringe 12 and to fit between a Luer 18 and a delivery end 20 of syringe 12. Generally, device 14 represents any type of connector used for interfacing enteral feeding components or other fluid delivery systems. Here, device 14 is sized to fit within the Luer 18 of syringe 12 at a first end and to form a sealed connection with syringe 12 from which fluid (medicine or food) flows. In the described embodiment, the delivery end 20 is a male connector end. Generally, device 14 can be formed to integrate other types of syringes including those with a female end. In such a case, end 22 of device 14 would be matingly received by a female end of the syringe that is sized to mate with end 22 of device 14.

Fluid delivery device 14 includes a female connector end 22 that overlaps the male portion of delivery end 20 of syringe 12 in the described embodiment. Delivery end 20 of syringe 12 and device 14 are permanently attached in the described embodiment. One embodiment of the fluid delivery system 10 includes a locking mechanism for permanent attachment of device 14 to syringe 12. The locking mechanism may be mechanical (e.g., a pin or barb that mechanically grabs the male end of the syringe) or chemical (e.g., an adhesive or bonding agent). A male connector end 24 of device 14 is sized to not mate with standard connectors or ports for I.V.'s as described before. Similarly, one embodiment of connector 16 includes a connecting end 34 that is sized to not engage or mate with standard I.V. ports and connectors.

Thus, fluid delivery device 14 is made especially for permanently connecting to an end of a syringe sized to meet ANSI/HIMA MD70.1 or ISO 594/1 and ISO 594/2 standards for intravenous ports and connectors to create a fluid delivery system that prevents inadvertent I.V. delivery of fluids intended for enteral delivery. For example, a syringe typically includes a male end for delivering fluid stored within a storage chamber of the syringe. As such, once a syringe is chosen for delivering fluids enterally instead of intravenously, permanent attachment of the fluid delivery device 14 reduces the likelihood of dangerous fluids being delivered intravenously. The fluid delivery system 10 comprises any known structure for permanently attaching, adhering or bonding the fluid delivery device 14 to the fluid delivery end of the syringe 12. To prevent the syringe with fluids not intended for intravenous delivery from being accidentally coupled to an intravenous fluid delivery port or connector, the fluid delivery device 14 is permanently attached to syringe 12 in the described embodiment of the fluid delivery system 10.

Generally, if a locking mechanism (mechanical structure or chemical element) is not used to make this permanent attachment, an application technique that permanently installs device 14 to a syringe, such as syringe 12, may be used, including spin welding and pressure mounting. In the described embodiment, the fluid delivery system includes, therefore, the syringe 12 (or other syringe), the fluid delivery device 14 permanently attached to syringe 12, connector 16 that is coupled to a tube 26, and the tube itself. The fluid delivery devices 14 and connector 16 each include fluid delivery ends sized to not mate with standard sized intravenous ports and connectors.

The fluid delivery system 10 comprises any known structure for permanently attaching, adhering or bonding the fluid delivery device to the fluid delivery end of the syringe in addition to those described. As such, one aspect of the embodiments of the invention is that, once a syringe is chosen for delivering fluids enterally instead of intravenously, a system and method includes permanent attachment of a fluid delivery device to a syringe to reduce the likelihood of dangerous fluids being delivered intravenously.

The embodiments of the locking mechanism include but are not limited to at least one a system that includes protruding locking tab, originating from a male end of device 14 to lock with an interior surface of the female connector end of connector 16. The female end of connector 16 is operably sized to receive and pass the male end of the device 14 only in a receiving direction.

While the fluid delivery device 14 may be made with any combination of male and female connectors as an input port, one described embodiment includes a female connector end 22 sized to receive and mate with a male end 20 of a syringe. The permanent attachment of the fluid delivery device 14 to the syringe 12 is particularly important since the male connector end of the permanently attached fluid delivery device is sized to meet ANSI/AAMI ID54:1996(R) 2005 for enteral delivery and not mate with ANSI/HIMA MD70.1 or ISO 594/1 and ISO 594/2 standards for intravenous ports and connectors. Thus, once an I.V. syringe is chosen for enteral delivery of food or medicine, it cannot accidentally be coupled to an I.V. port to accidentally introduce dangerous fluids to the blood stream. Moreover, the female connector end of the connector 16 defines an outer dimension or size made to fit within and engage with a protruding flange (Luer) that surrounds the protruding male end of the syringe to support the permanent and sealed attachment to the syringe.

One embodiment of the fluid delivery device 14 includes a female connector end having an outer diameter that is sized to matingly fit within a port of a syringe of a second size. For example, I.V. syringes typically are made in one of two sizes. Thus, an alternative fluid delivery system includes a fluid delivery device 14 that is formed to matingly be received by a male end of a syringe having an outer diameter of a first size (or type) which is typically for I.V. applications and to also matingly fit into a male end of a second type of syringe for enteral delivery of food and medicine defining an inner diameter of a second size.

Thus, the embodiments of the invention for fluid delivery systems include a syringe 12 having a chamber for temporarily holding a fluid intended for enteral delivery to a patient and a permanently attached fluid delivery device fluidly connected to the chamber for delivering the fluid to a tube wherein the male connector end of the fluid delivery device is sized to meet ANSI/AAMI ID54:1996(R) 2005 and not mate with ANSI/HIMA MD70.1 or ISO 594/1 and ISO 594/2 standards for intravenous ports and connectors.

Additionally, in the embodiment of FIG. 1, male end 24 includes a locking tab 28 sized to engage a corresponding channel 30 when aligned with channel 30. Accordingly, one function of tab 28 is to prevent connection of any device or connected not configured to connect and couple to connector 16 (which is specifically made according to the aforementioned enteral feeding standards for enteral feeding). As may be seen, connector 16 includes a female end further includes a locking region 32 sized to hold locking tab 28 when device 14 is rotated to cause tab 24 to rotate into locking region 32. As such, locking tab 28 performs the function of preventing misconnections between devices not intended to be interconnected, to only allow device 14 to be mated with specific interconnecting members such as connector 16 that have a channel 30, and a locking region 32 to lock the device 14 to connector 16 and to allow such devices to remain attached as long as desired.

FIGS. 2A and 2B illustrate additional details of a locking mechanism of fluid delivery system 10 formed according to one embodiment of the invention. As described in relation to FIG. 1, a fluid delivery device 14 includes an end 24 that includes a locking tab 28. End 24 is sized and configured to engage a connector 16, and more specifically, a female connector end 34 of connector 16. As described before, locking tab 28, when properly aligned, slides along the channel 30 when end 24 is inserted into end 34 of connector 16 and is configured to lock with connector 16 when turned into a locking position such that tab 28 rotates into locking region 32. FIG. 2A illustrates a side view of a portion of fluid delivery system 10. FIG. 2B, on the other hand, illustrates a front view of connector 16. As may be seen, locking tab 28, in this embodiment, is relatively narrow and is much more narrow than a width of locking region 32 (whose relative width is illustrated by the dashed line).

FIGS. 3A and 3B illustrate additional details of a fluid delivery system 10 formed according to one embodiment of the invention. As described in relation to FIG. 1, a device 14 includes an end 24 that includes a locking tab 28. End 24 is configured to engage a connector 16, and more specifically, a connector end 14 of connector 16. As described before, locking tab 28, when properly aligned, slides along the channel 30 when end 24 is inserted into end 34 of device 16 and then is turned into a locking position into locking region 32. More specifically, FIG. 3A illustrates a side view of fluid delivery system 10. FIG. 3B, on the other hand, illustrates a front view of connector 16. As may be seen, locking tab 28, in this embodiment of FIGS. 3A and 3B, is relatively narrow and is much more narrow (less than ½ of the width) than a width of locking region 32\. It should also be noted that an axial length of locking tab 28 of FIGS. 3A-B is much shorter (less than half) in relation to locking tab 28 of FIGS. 1-2.

FIGS. 4A and 4B illustrate additional details of a fluid delivery system 50 formed according to one embodiment of the invention. As described in relation to FIG. 1, a fluid delivery device 14 includes an end 24 that includes a locking tab 28. Here in FIGS. 4A and 4B, however, end 24 includes two tabs 28 disposed on opposite sides of end 24 of device 14. As before, device 24 is configured to engage a connector 16, and more specifically, a connector end 34 of connector 16. Here, however, locking tabs 28, when properly aligned, slide along the two channels 30 that also are disposed on opposite sides of end 34 of device 16. Accordingly, when end 24 is inserted into end 34 of device 16 and then is turned into a locking position in locking regions 32.

FIG. 4A illustrates a side view of fluid delivery system 50. FIG. 4B, on the other hand, illustrates a front view of this embodiment of device 16. As may be seen, locking tabs 28, in this embodiment, are relatively narrow and is much more narrow than a width of locking region 32 and are the approximate length of the embodiments of FIGS. 1 and 2. The axial length of tabs 28 are between ¼ and ½ of the length of end 24 in these embodiments while the length of tab 28 in the embodiment if FIGS. 3A and 3B is less than one half of the length of the tabs 28 of the embodiments of FIGS. 1, 2 and 4.

FIGS. 5A and 5B illustrate additional details of a fluid delivery system 52 formed according to one embodiment of the invention. As described in relation to other figures including FIG. 1-4B, a device 14 includes an end 24 that includes at least one locking tab 28. In this embodiment, however, end 24 includes four tabs 28 configured to engage end 34 of device 16. Additionally, device 16 of defines four channels 30 configured to receive locking tabs 28 and four locking regions 32 configured to receive and hold locking tabs 28 when connector device 14 is rotated so that tabs 28 slide into their corresponding locking regions 32, respectively. For each embodiment including this one, the channels 30 are disposed and configured to correspond to the sizing and arrangement of the locking tabs of the various ends 24.

Figure 6A:
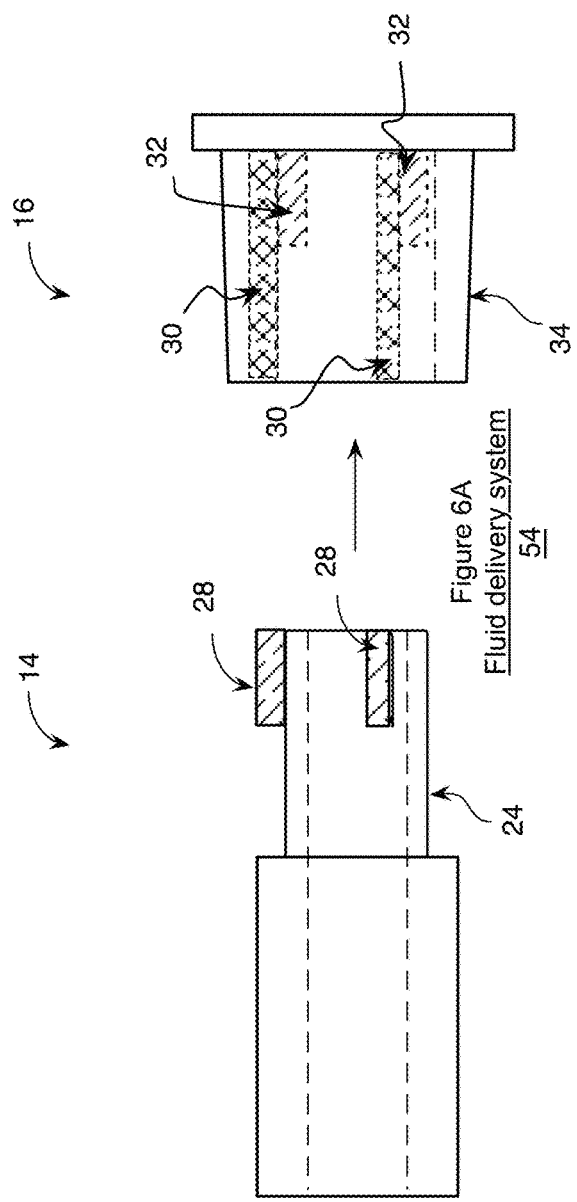
FIGS. 6A and 6B illustrate additional details of a fluid delivery system 54 formed according to one embodiment of the invention.
Figure 6B:
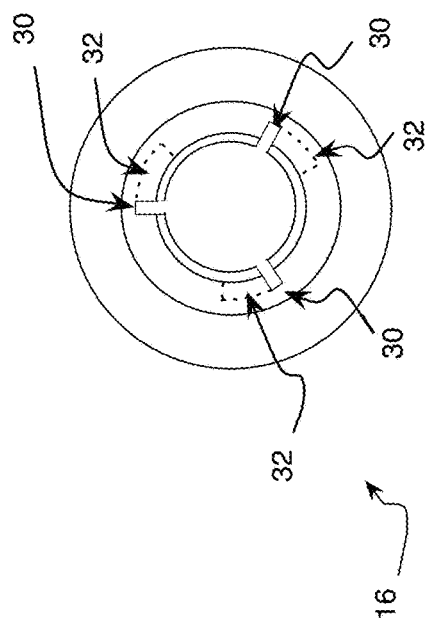

FIGS. 6A and 6B illustrate additional details of a fluid delivery system 54 formed according to one embodiment of the invention. As described in relation to FIGS. 5A-5B, a device 14 includes an end 24 that includes at least one locking tab 28. In this embodiment, however, end 24 includes three tabs 28 configured to engage end 34 of device 16. Additionally, device 16 of defines three channels 30 configured to receive locking tabs 28 and three locking regions 32 configured to receive and hold locking tabs 28 when connector device 14 is rotated so that tabs 28 slide into their corresponding locking regions 32, respectively. The three locking tabs, in this embodiment are separated radially by 120 degrees about an end surface of end 174 (which is circular in shape).

Generally, each embodiment of the above figures illustrates that the locking regions are formed in an area that is radially to the right of a corresponding channel that receives the locking tab. Alternatively, the locking regions may be disposed on a radially left side of the channels that receive the locking tabs.

FIGS. 7-9 illustrate example alternatives to shapes of the locking tabs 28 of ends 24 and corresponding channels of device 16 that receive the locking tabs 28. The figures illustrate that the tabs and corresponding channels may vary in length and width. In the described embodiments, the channels comprise a width to match a thickness of the tabs 28. The locking regions define an axial depth that matches the axial length of the tabs 28. Generally, an axially shorter tab may typically have a greater thickness (width). The corresponding locking regions will have a depth and width configured to engage the locking tab. For example, in FIG. 7, the locking tab 28 in fluid delivery system 60 is short and wide (as seen from a front view of channel 30 of device 16 of FIG. 7). Conversely, in FIG. 8, the locking tab of fluid delivery system 62 is long and nearly extends the length of end 24 and is the most narrow (as seen from a front view of channel 30 of device 16 of the embodiment of FIG. 8). FIG. 9 shows a locking tab 28 of fluid delivery system 64 that is but much shorter than tab 28 of FIG. 7 and is also a little thicker or wider than tab 28 of FIG. 7.

Figure 11:
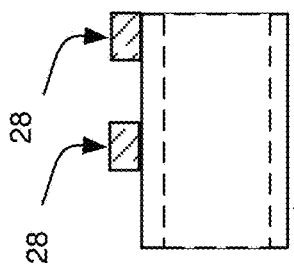
FIGS. 10-15 are side views of various alternative embodiments of fluid device deliver ends and locking tabs and their relative positions on fluid device deliver ends.
Figure 12:
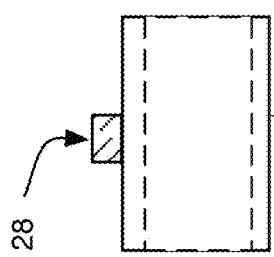
Figure 10:
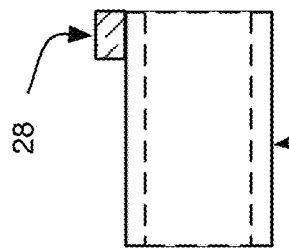
Figure 15:
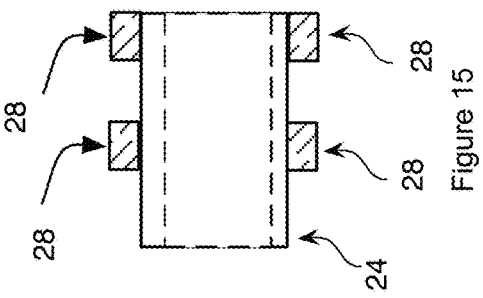
Figure 14:
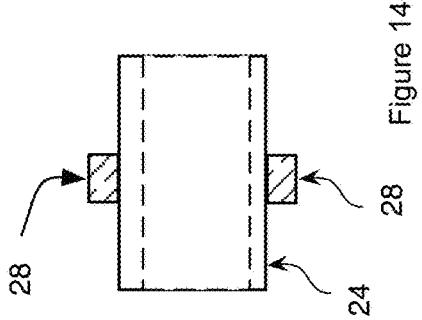
Figure 13:
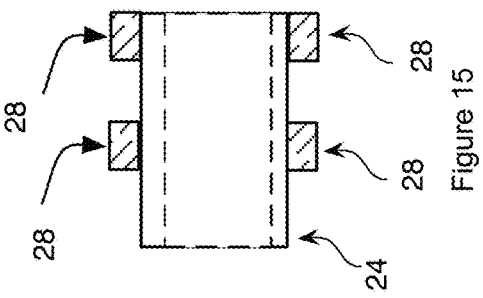

FIGS. 10-15 are side views of various alternative embodiments of an end 24 and locking tabs 28 and their relative positions on end 24. FIG. 10 illustrates a single locking tab 28 placed at an end of end 24 of a fluid device 14. FIG. 11 illustrates that a single locking tab may be placed any where (e.g., the axial middle) of end 24 and that the locking tab 28 does not need to be at the end. FIG. 12 illustrates that multiple locking tabs 322 may be disposed in axial alignment on a surface of end 24 wherein one of the locking tabs is at the end or near the end of end 24. Alternatively, the locking tabs do not need to be axially aligned. FIG. 13 illustrates two locking tabs 28 are disposed on opposite sides of end 24 disposed near an end of end 24. FIG. 14 illustrates two locking tabs 28 on opposite sides of end 24 near an axial middle of end 24. FIG. 15 illustrates two locking tabs 28 on opposite sides of end 24 near an end of end 24 and two locking tabs 28 on opposite sides of end 24 near an axial middle of end 24. One advantage of axially aligning locking tabs such as shown in FIGS. 12 and 14 is that one channel within device 132 may receive both locking axially aligned tabs 28 until the device 24 is fully inserted into device 16 and rotated to cause the locking tabs 28 to lock into the associated or corresponding locking regions 32. It should be understood that, while not shown here, each receiving connector includes at least one channel and a locking region 32 configured to receive the locking tab(s) 28.

Figure 16:
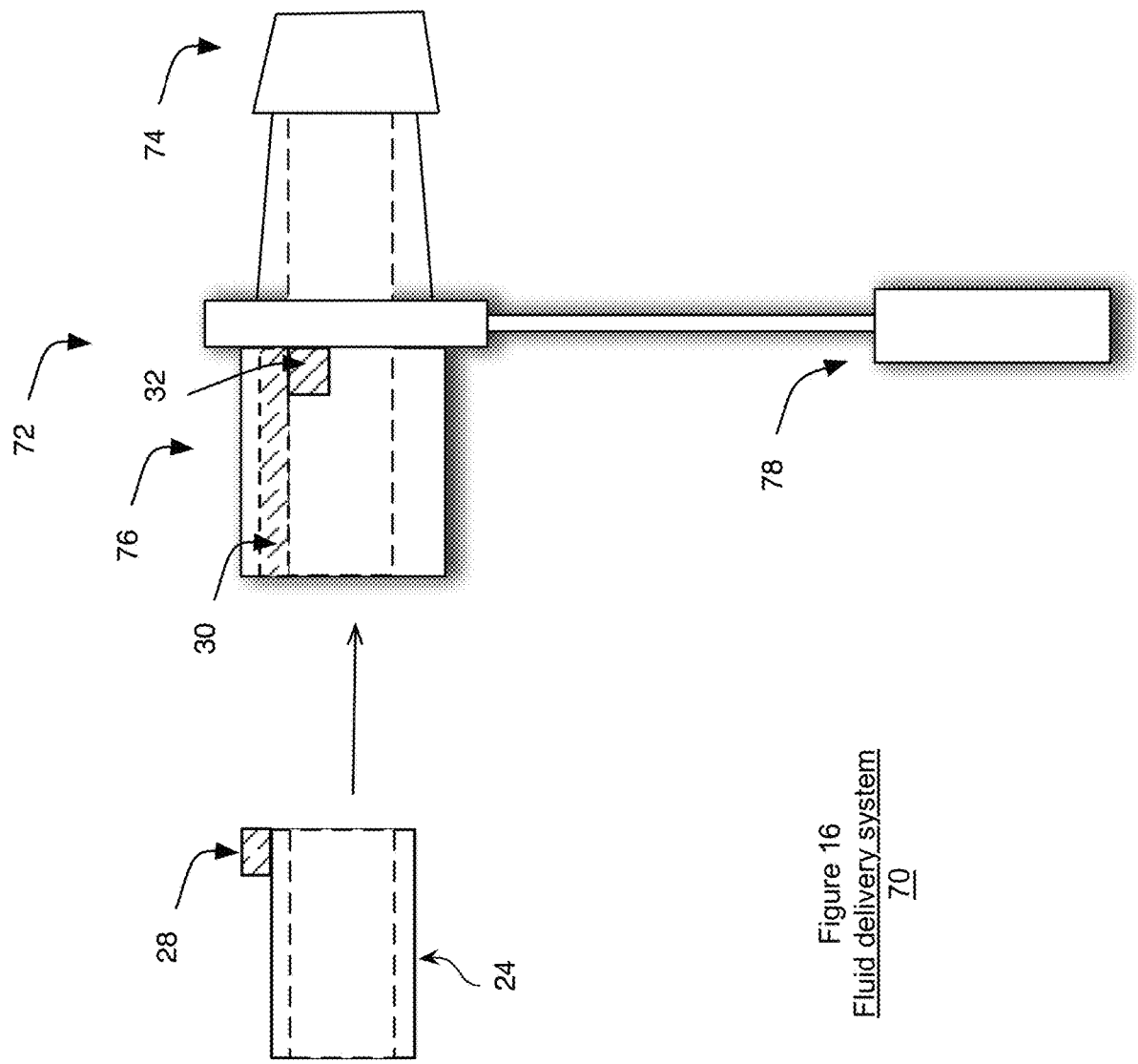
FIG. 16 is a diagram illustrating a layout of a feeding system including a feeding cap according to one embodiment of the invention.

FIG. 16 is a diagram illustrating a layout of a feeding system including a feeding cap according to one embodiment of the invention. As may be seen, a fluid delivery system 70 includes a feeding cap 72 that includes an output end 74 (barbed male end), a receiving end 76 (female end) and a permanently attached cap 78. Cap 78 is sized to fit over end 76.

One important aspect is that the receiving end of the feeding cap 72 is sized to not allow a syringe for I.V. applications with a Luer connector to matingly engage the feeding cap. Additionally, an opening within end 76 for receiving a male end 24 is sized to be larger than an I.V. syringe male end having a smaller standard diameter (first type of syringe) for I.V. syringes and is further sized to be smaller than the larger standard diameter (second type of syringe) for I.V. syringes. More generally, the opening is sized to not matingly engage any male end of a syringe for I.V. applications. On the other hand, the input port of end 76 of the feeding cap 72 is sized to receive and engage the output end of the fluid delivery devices for enteral applications including, for example, fluid delivery device 14 of any of the preceding figures.

As described before, a locking tab 28 is used on any mating device that is configured to fit within and slide along a channel 30 and to lock into place into a locking region 32. Any of the configurations and embodiments described before may be used here with the system 70 including modifications in arrangement and size of the locking tabs and the numbers of locking tabs and associated channels and locking regions.

It should be understood end 24 may be an end of fluid delivery device 14 that attaches to a syringe. End 24 may also be the end of any other device. As such, such an end may be formed directly on a syringe, on a connector of a feeding system that in turn is connected to a hose, or to any device having an end that is intended to connect to end 76 of feeding cap 72 or to any connector such as connector 16 described in the previous figures. One important aspect is that many different configurations may utilize the connectors that are sized as described herein or connectors that have a locking system similar to any of those of the present disclosure.

FIGS. 17-19 are perspective views of ends 24 of fluid delivery devices with alternative embodiments of locking tabs 28. Locking tabs may be axially aligned to the end 24 or perpendicular to the axial center of end 24 as shown in FIG. 19.

FIG. 20 is an alternative embodiment of the invention of a syringe with an integral locking tab for coupling to a connector in a fluid delivery system. It should be understood that end 24 of syringe 82 may be configured similar to any of the embodiments illustrated in relation to ends 24 of any fluid delivery device 14 shown in the preceding figures. In this particular embodiment, syringe 82 is an enteral feeding syringe configured to conform with enteral feeding standards cited herein. The locking tab 28 will not only help prevent misconnections, but also allow the syringe to be locked into connector 16 for enteral feeding. As before, tab 28 is configured and sized to engage connector 16 with channel 30 and locking region 32 of connector 16. Connector 16 in this embodiment, in turn, is connected to a tube 26 which in turn is connected to a fluid delivery device 14 that is configured as described before but is connected to a tube instead of an IV Syringe. Device 14, in turn, connects to a second connector 16 that in turn is connected to a second tube 26.

FIG. 21 is an alternative embodiment of an enteral feeding system that includes a syringe that includes a barbed connector configured to receive a tube having an overmolded end. A system 84 includes a syringe 86 that includes a barbed connector 88 that connects to overmold region 90 of tube 26 at a first end of tube 26. The barbed connector 94 of syringe 86 is configured to receive tube 26 with an overmold (overmolded end) that slides over the barbed connector of end 88 or a tube 26 that slides into end 88 as described in relation to the first tube 26 of FIG. 22 and the manner in which it slides into device 14. A second end of the first tube 26 also connects to device 14 similarly which in turn connects to a connector 16 that in turn is connected to a second tube 26. FIGS. 22-23 illustrate one aspect which is that the various devices described herein may be configured to operate with each other in many different configurations without departing from the scope of the disclosure.

FIGS. 22, 23 and 24 illustrate an alternative embodiment of the invention a connector with at least one stop flange. As described in relation to other figures including FIG. 1, a fluid delivery device 94 includes an end 24 that includes at least one locking tab 28. End 24 is configured to engage a connector 16, and more specifically, a connector end 34 of connector 16. As described before, each locking tab 28, when properly aligned, slides along the channels 30 when end 24 is inserted into end 34 of device 16 and then is turned into a locking position in locking regions 32. Device 94 and 16 generally are for enteral feeding purposes according to one embodiment of the invention but can generally be used for any fluid delivery system. More specifically, FIG. 22 illustrates a side view of fluid delivery system 92. One aspect of device 94, however, is that device 94 includes a stop flange 96. Stop flange 96 is placed long end 24 such that when end 34 of device 16 hits or abuts stop flange 96, tabs 28 align with locking areas 32 so that the connector may be easily rotated into a locked position.

FIGS. 23 and 24, on the other hand, illustrate front views of device 94 with alternative designs for the stop flange. As may be seen, the locking tab 28, in this embodiment, are relatively narrow and is much more narrow than a width of locking region 32. Additionally, as may be seen, the fluid delivery devices here include four locking tabs and connectors 16 include four channels 30 and locking areas 32. In FIG. 23, stop flange 99a is disk shaped (circular). In FIG. 24, however, a plurality of stop flanges 99b extend outwardly from a radial axis of device 94. While four stop flanges 99b are shown, it should be understood that a lesser or greater number of stop flanges may be used.

In one embodiment of the disclosure, a fluid delivery system includes a first fluid delivery end formed on one of a syringe or a fluid delivery device that further comprises sizing that meets enteral feeding standards including ANSI/AAMI ID54:1996(R) 2005 and not mate with standards for intravenous ports and connectors including ANSI/HIMA MD70.1, ISO 594/1 and ISO 594/2; and at least one locking tab. The system further includes a connector for enteral feeding for delivering fluids to a patent via a connected tube, wherein the connector further comprises a fluid receiving end that meets enteral feeding standards including ANSI/AAMI ID54:1996(R) 2005 and not mate with standards for intravenous ports and connectors including ANSI/HIMA MD70.1, ISO 594/1 and ISO 594/2. The connector further includes at least one channel for receiving the at least one locking tab of the fluid delivery end when the fluid delivery end is inserted into fluid receiving end and a locking region configured to receive the locking tab and to hold the fluid delivery end when the fluid delivery end is inserted and rotated into a locking position.

While the previous embodiment is described in relation to a feeding system, the above configurations may readily be modified for other medical uses such as, for example, a catheter. In general, the described embodiments may be utilized in any system in which it is desirable to avoid misconnections and advantageous to have a locking system.

FIG. 25 is an enteral feeding system 100 that includes a syringe and a syringe adaptor according to one embodiment of the invention. Referring to FIG. 25, enteral feeding system 100 includes a syringe 102 that is configured to receive an adaptor 104. As may be seen, syringe 102 includes a threaded passageway 106 that is configured to securely receive adaptor 104. Adaptor 104 includes a threaded portion 26 that is configured to allow adaptor 104 to be screwed into syringe 102 and to engage the threaded passageway 106 of syringe 102.

Adaptor 104 includes an outwardly extending body 110 that further has a first outwardly extending adaptor connector 112 and a second outwardly extending adaptor connector 114 that extend outwardly from outwardly extending body 110. At least one of the outwardly extending connectors 112 and 114, in one embodiment, is sized to meet ANSI/AAMI ID54:1996(R) 2005 and not mate with ANSI/HIMA MD70.1 or ISO 594/1 and ISO 594/2 standards for intravenous ports and connectors.

Outwardly extending body 110 is for conducting fluid (e.g., food) between a cavity defined by syringe 102 and at least one of the outwardly extending adaptor connectors 112 and 114. As may further be seen, system 100 includes a stop cock 116 for inserting into one of the outwardly extending adaptor connectors 112 and 114. As may further be seen, system 100 includes a tube 118 that couples to either connector 112 or connector 114.

FIG. 26 is an enteral feeding system 120 that includes a syringe and a syringe adaptor according to one embodiment of the invention. Referring to FIG. 26, enteral feeding system 120 includes a syringe 102 that is configured to receive an adaptor 122. As may be seen, syringe 102 includes threaded passageway 106 that is configured to securely receive adaptor 122. Adaptor 122 includes a threaded portion 124 that is configured to allow adaptor 122 to be screwed into syringe 102 and to engage threaded passageway 106.

Adaptor 122 includes a first outwardly extending adaptor connector 126 and a second outwardly extending adaptor connector 128 that extend outwardly from a base of adaptor 122. The body of adaptor 122 is configured to conduct fluid (e.g., food) between a cavity defined by syringe 102 and at least one of the outwardly extending adaptor connectors 126 and 128. As may further be seen, system 100 includes a stop cock 116 for inserting into one of the outwardly extending adaptor connectors 126 and 128 and into enteral feeding tube 118. As may further be seen, system 100 includes a tube 118 that couples to either connector 126 or connector 128.

FIG. 27 is an enteral feeding system 130 that includes a syringe and a syringe adaptor according to one embodiment of the invention. Referring to FIG. 28, enteral feeding system 130 includes a syringe 132 that is configured to receive an adaptor 134. As may be seen, syringe 132 includes a threaded passageway 136 that is configured to securely receive adaptor 134. Adaptor 134 includes a threaded portion (not shown) that is configured to allow adaptor 134 to be screwed onto syringe 132. Adaptor 134 further includes a male receiving port 138 configured to engage syringe 132 to receive fluids from syringe 132.

Adaptor 122 includes a first outwardly extending adaptor connector 140 and a second outwardly 142 that extend from connector 134. Adaptor connectors 140 and 142 extend outwardly from a base of adaptor 134. The base of adaptor 134 is configured to conduct fluid (e.g., food) between a cavity defined by syringe 132 and at least one of the outwardly extending adaptor connectors 140 and 142 and into enteral feeding tube 118. As may further be seen, system 130 includes a stop cock 116 for inserting into one of the outwardly extending adaptor connectors 140 and 142.

FIG. 28 is an enteral feeding system 130 that includes a syringe and a syringe adaptor according to one embodiment of the invention. Referring to FIG. 28, enteral feeding system 150 includes a syringe 152 that is configured to receive an adaptor 154. Syringe 152 includes a threaded passageway 156 that is configured to securely receive adaptor 154. Adaptor 154 includes a threaded portion 158 that is configured to allow adaptor 134 to be screwed into passageway 156 of syringe 152. Adaptor 154 is configured to engage syringe 152 to receive fluids from syringe 152.

Adaptor 154 includes a first outwardly extending adaptor connector 160 and a second outwardly 162 that extend from adapter 154. Adaptor connectors 160 and 162 extend outwardly from adaptor 154. Adaptor 154 is configured to conduct fluid (e.g., food) between a cavity defined by syringe 152 and at least one of the outwardly extending adaptor connectors 160 and 162 and into enteral feeding tube 118. As may further be seen, system 130 includes a stop cock 116 for inserting into one of the outwardly extending adaptor connectors 140 and 142.

FIG. 29 is an enteral feeding system 130 that includes a syringe and a syringe adaptor according to one embodiment of the invention. Referring to FIG. 29, enteral feeding system 150 includes a syringe 152 that is configured to receive an adaptor 154. Syringe 152 includes a threaded passageway 156 that is similar to a screw connector with threads that are disposed on an outer surface of threaded passageway 156 and that is configured to securely receive adaptor 154. Adaptor 154 includes a threaded portion 158 with threads 158 on an inner surface and that is configured to allow adaptor 134 to be screwed onto passageway 156 of syringe 152. Adaptor 154 is configured to engage syringe 152 to receive fluids from syringe 152.

Adaptor 154 includes a first outwardly extending adaptor connector 160 and a second outwardly extending adaptor connector 162 that extend from connector 154. Adaptor connectors 160 and 162 extend outwardly from adaptor 134. Adaptor 134 is configured to conduct fluid (e.g., food) between a cavity defined by syringe 152 and at least one of the outwardly extending adaptor connectors 160 and 162 and into enteral feeding tube 118. As may further be seen, system 130 includes a stop cock 116 for inserting into one of the outwardly extending adaptor connectors 140 and 142.

One difference between the systems of FIGS. 29 and 30 is the threading of the syringe and the adapter. Here in FIG. 30, the adapter screws over the threads of passageway 156. In one embodiment, syringe 152 is a standard I.V. syringe for delivery of medicine to a patient with a standard threaded screw connector.

FIG. 30 is an embodiment of an adapter for enteral feeding according to one embodiment of the invention. An adaptor 110 includes two connectors, namely connectors 112 and 114. The dashed lines indicate the internal passageways through which liquid flows. The internal passageways may be configured according to designer preference. Generally, at least one of the connectors 112 and 114 and the tubes 118 (not shown here) are sized to support a desired flow rate. Additionally, it should be noted that the two connectors 112 and 114 are not the same length.

The two connectors 112 and 114 do not need to be the same diameter with the same flow rate. If, for example, connector 114 is coupled to a feeding tube 118, connector 112 may be inserted into the fluid to be fed to the patient and drawn into the syringe when a syringe plunger is pulled away from the adapter to create a suction. Having a longer connector is advantageous in that it facilitates insertion into the fluid to be fed to the patient. In the illustrated embodiment, the two connectors have different lengths but similar diameters. In an alternative embodiment, connector 112 has a greater diameter that connector 114 to facilitate drawing fluid into the syringe. These aspects of adapter 110 may be utilized with any of the previously described adaptors.

Figure 31:
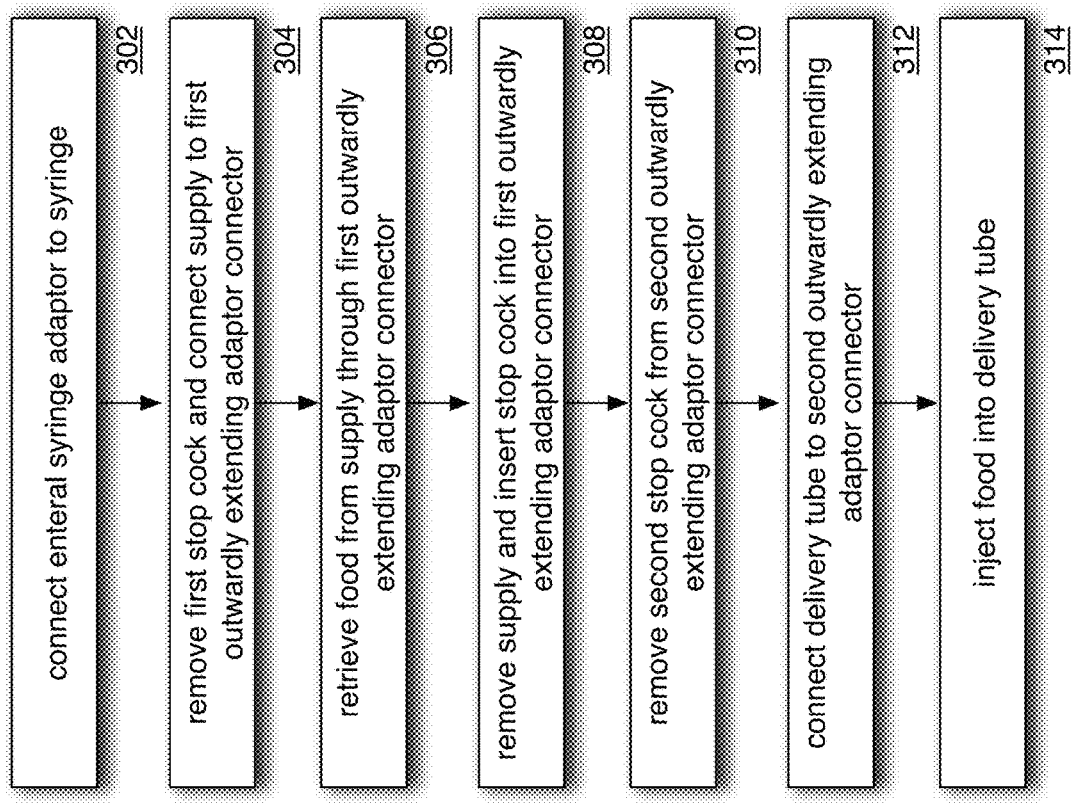
FIG. 31 is a flow chart that illustrates a method that corresponds to the enteral systems of the embodiments of the present invention.

FIG. 31 is a flow chart that illustrates a method that corresponds to the enteral systems of the embodiments of the present invention. The method commences with connecting an enteral syringe adaptor to an enteral syringe (302). Generally, different patients can receive food enterally at different flow rates. Accordingly, if a plurality of adapters having different flow rates defined by a diameter of the connectors of the adapter and the corresponding feeding tube sizes. The method further includes removing a first stop cock and connecting a supply to a first outwardly extending adaptor connector (304). Thereafter, the method includes retrieving food from the supply through first outwardly extending adaptor connector (306). Thereafter, the me method includes removing the supply and inserting the stop cock into first outwardly extending adaptor connector (308).

The preceding steps relate to obtaining fluid for feeding into the enteral syringe. The following steps relate to feeding the patient. It should be noted that some steps of the following method may occur in earlier in the process and are not required to be in the sequential order shown. The method includes removing a second stop cock from second outwardly extending adaptor connector (310) and connecting a delivery tube to second outwardly extending adaptor connector (312). The method concludes with inject fluid (food) into a delivery tube (314) to enterally feed the patient. The flow rate is limited to a diameter of the delivery tube. The adapter and corresponding delivery tube are chosen from a plurality of adaptors that support different flow rates according to patient needs.

FIG. 32 is an embodiment of an enteral feeding system that includes a feeding pouch and adaptor. As may be seen an enteral feeding system 320 includes a feeding pouch 322 that further includes a port 324 for dispensing food or the contents of pouch 322. Pouch 322 further includes an air port 326 to allow the contents to drain when opened. Pouch 328 further includes an eyelet 328 to allow the pouch to be hung. Adaptor 124, as previously described, is threaded and configured to mate with and screw into threads 106 formed within port 324. Adapter 124 further includes ports 126 and 128 for coupling to a feeding tube 118. A stop cock 116 may be used to seal an unused port 126 or 128.

FIG. 33 illustrates an alternative embodiment of the invention of an adaptor. As may be seen, enteral feeding adaptor 330 includes only one port 126 or 128.

FIG. 34 is an embodiment of an enteral feeding system that includes a feeding pouch and adaptor. As may be seen an enteral feeding system 340 includes a feeding pouch 322 that further includes a port 342 for dispensing food or the contents of pouch 322. Port 154 comprises a screw type connector with threads on an external surface of the passageway or port. Pouch 322 further includes an air port 326 to allow the contents to drain when opened. Pouch 328 further includes an eyelet 328 to allow the pouch to be hung.

Adaptor 154, as previously described, is threaded and configured to mate with and screw onto threads 106 formed within port 324. Adapter 124 further includes ports 126 and 128 for coupling to a feeding tube 118. A stop cock 116 may be used to seal an unused port 126 or 128.

Adaptor 154 includes a threaded passageway that is similar to a screw connector with threads 158 on an inner surface and that is configured to allow adaptor 154 to be screwed onto port 342. Adaptor 154 is configured to engage port 342 to receive fluids for delivery to a patient via enteral feeding tube 118.

Adaptor 154 includes a first outwardly extending adaptor connector 160 and a second outwardly extending adaptor connector 162 that extend from connector 154. Adaptor connectors 160 and 162 extend outwardly from adaptor 134. Adaptor 134 is configured to conduct fluid (e.g., food) between a cavity defined by syringe 152 and at least one of the outwardly extending adaptor connectors 160 and 162 and into enteral feeding tube 118. As may further be seen, system 130 includes a stop cock 116 for inserting into one of the outwardly extending adaptor connectors 140 and 142.

FIG. 35 is an enteral feeding system with a pouch, an adapter and an enteral connector according to one embodiment of the invention. Enteral feeding system 350 includes a feeding pouch 322 that further includes a port 352 for dispensing food or the contents of pouch 322. Port 352 comprises a screw type connector with threads 354 on an external surface of the passageway or port 352. Pouch 322 further includes an air port 326 to allow the contents to drain when opened. Pouch 322 further includes an eyelet 328 to allow the pouch to be hung.

Adaptor 356, as previously described, is threaded and configured to mate with and screw onto threads 352 of port 324. Adapter 356 further includes ports 358 and 360. Port 358 is for receiving fluids from another supply (e.g., medicine from a syringe or supply line) that is to be delivered to the patient enterally. Port 360 is for coupling to a tube 362. A stop cock 116 may be used to seal port 358.

Adaptor 356 includes a threaded passageway 156 that is similar to a screw connector with threads 158 on an inner surface and that is configured to allow adaptor 356 to be screwed onto port 352. Adaptor 356 is configured to engage port 352 to receive fluids for delivery to a patient via an enteral feeding tube.

Tube 362 terminates into an enteral connector 364. Enteral connector 364 is generally formed to comport with ANSI/AAMI ID54:1996(R) 2005 (or subsequent versions) for enteral feeding. Additionally, in the embodiment of FIG. 11, connector 364 includes a locking tab 366 sized to engage a corresponding channel 368 of an enteral connector 370 when aligned with channel 368. Accordingly, one function of tab 366 is to prevent connection of device 364 and connectors other than connector 370 (which is specifically made according to the aforementioned enteral feeding standards for enteral feeding). As may be seen, connector 370 further includes a locking region 372 sized to hold locking tab 366 when device 364 is rotated to cause tab 366 to rotate into locking region 372. As such, locking tab 366 performs the function of preventing misconnections between devices not intended to be interconnected, to only allow device 158 to be mated with specific interconnecting members such as connector 370 that have a channel 368, and to lock the device 364 to connector 370. Connector 370 is coupled to tube 374 which is an enteral feeding tube.

FIG. 36 is an enteral feeding system 400 that includes a syringe with a contiguously formed feeding tube according to one embodiment of the invention. Referring to FIG. 12, enteral feeding system 400 includes a syringe 402 that is extruded to contiguously have an enteral feeding tube 404 for enteral feeding purposes. In an alternative embodiment, feeding tube 404 terminates in a connector configured to mate with another connector as described in relation to FIG. 13 below. The connector may be, but is not required to be, a locking connector. Such a system may readily be combined with any other element disclosed herein.

FIG. 37 is an enteral feeding system 450 that includes a syringe and a syringe adaptor according to one embodiment of the invention. Referring to FIG. 13, enteral feeding system 450 includes a syringe 452 that is configured to receive an adaptor 454. As may be seen, syringe 452 includes a threaded passageway 456 that is configured to securely receive adaptor 454. Adaptor 454 includes a threaded portion 458 that is configured to allow adaptor 454 to be screwed into syringe 452 and to engage the threaded passageway 456 of syringe 452.

Adaptor 454 includes an outwardly extending body 460 that that is extruded to contiguously have an enteral feeding tube 462 for enteral feeding purposes. In one embodiment, feeding tube 462 is configured, similar to feeding tube 404, to be inserted into the patient for feeding. In the described embodiment, however, feeding tube 462 terminates in a locking connector that is similar to the locking connector system of FIG. 11. Specifically, feeding tube 462 terminates in a connector 364 that includes a locking tab 366 sized to engage a corresponding channel 368 of an enteral connector 370 when aligned with channel 368. Accordingly, one function of tab 366 is to prevent connection of device 364 and connectors other than connector 370 (which is specifically made according to the aforementioned enteral feeding standards for enteral feeding). As may be seen, connector 370 further includes a locking region 372 sized to hold locking tab 366 when device 364 is rotated to cause tab 366 to rotate into locking region 372. As such, locking tab 366 performs the function of preventing misconnections between devices not intended to be interconnected, to only allow device 158 to be mated with specific interconnecting members such as connector 370 that have a channel 368, and to lock the device 364 to connector 370. Connector 370 is coupled to tube 374 which is an enteral feeding tube. It should be noted that in a configuration such as that shown here in FIG. 13, that tube 462 may, alternatively, be a tube that is not an enteral feeding tube since it terminates into a connector. Further, while a locking connector with a single tab is shown here, any connector with any number of locking tabs or any known locking mechanism may be used. Reference herein to locking connector includes all such embodiments. Further aspects of the disclosure may be seen in the following examples.

Example 1

An enteral feeding system, comprising:
a syringe that defines a chamber for holding fluids and a syringe output port wherein the syringe output port further includes a threaded portion;
an adapter that includes a threaded portion sized and configured to mate with the threaded portion of the syringe output port, wherein:
the adapter includes at least two output ports and, more specifically, includes first and second output ports;
at least one of the first and second output ports is sized in accordance with enteral feeding standards; and
the first and second output ports each define a passageway that is coupled to a passageway of the adapter.

Example 2

The enteral feeding system of example 1 wherein the first output port has a greater length than the second output port.

Example 3

The enteral feeding system of example 1 wherein the first output port has a greater diameter than the second output port.

Example 4

The enteral feeding system of example 1 wherein the first and second output ports, along with a body of the adaptor, form a y-connector.

Example 5

An enteral feeding system, comprising:
a feeding pouch that further includes a delivery port wherein the delivery port includes threads on one of an outer or an inner surface; and
an adapter that includes a delivery port that couples to a tube and further includes threads on one of an inner or an other surface and configured to mate with a screw with the threads of the delivery port of the feeding pouch.

Example 6

The system of example 5 wherein the adapter includes two ports.

Example 7

The system of example 6 wherein both ports extend in a direction away from a receiving port of the adapter that receives fluid from the pouch.

Example 8

The system of example 6 wherein one port extends in a direction away from a receiving port of the adapter that receives fluid from the pouch and one port extends upward when the adapter is attached to the pouch and the pouch is hanging to allow the fluid to flow.

Example 9

The system of example 5 wherein the delivery port of the adapter is coupled to a tube that is further coupled to a first enteral feeding connector.

Example 10

The system of example 9 wherein the first feeding connector couples to a second enteral feeding connector that is coupled to an enteral feeding tube.

Example 11

The system of example 10 wherein the first and second enteral feeding connector are configured to lock to each other.

Example 12

An enteral feeding system, comprising:
a syringe that defines a chamber for holding fluids and a syringe output port wherein the syringe output port further includes a threaded portion; and
an adapter that includes a threaded portion sized and configured to mate with the threaded portion of the syringe output port, wherein:
the adapter includes a contiguously extruded portion that terminates in an enteral feeding tube.

Example 13

The enteral feeding system of example 12 wherein the feeding tube terminates in a connector configured to mate with a second connector.

Example 14

The enteral feeding system of example 13 wherein the second connector is connected to an enteral feeding tube.

Example 15

The enteral feeding system of example 13 wherein the connector and the second connector are locking connectors and are configured to engage and lock with each other.

Example 16

An enteral feeding system, comprising:
a syringe that defines a chamber for holding fluids and a syringe output port wherein the syringe output port that includes a contiguously extruded portion that terminates in an enteral feeding tube.

Example 17

The enteral feeding system of example 16 wherein the feeding tube terminates in a connector configured to mate with a second connector.

Example 18

The enteral feeding system of example 17 wherein the second connector is connected to an enteral feeding tube.

Example 19

The enteral feeding system of example 17 wherein the connector and the second connector are locking connectors and are configured to engage and lock with each other.

While the invention is susceptible to various modifications and alternative forms, specific embodiments thereof have been shown by way of example in the drawings and detailed description. It should be understood, however, that the drawings and detailed description thereto are not intended to limit the invention to the particular form disclosed, but, on the contrary, the invention is to cover all modifications, equivalents and alternatives falling within the spirit and scope of the present invention as defined by the claims. As may be seen, the described embodiments may be modified in many different ways without departing from the scope or teachings of the invention.

What is claimed is:
1. A fluid delivery system, comprising:
a first fluid delivery end formed on one of a syringe or a fluid delivery device that further comprises:
sizing that meets enteral feeding standards including ANSI/AAMI ID54:1996(R) 2005 and not mate with standards for intravenous ports and connectors including ANSI/HIMA MD70.1, ISO 594/1 and ISO 594/2; and
at least one axially aligned locking tab; and
a connector for enteral feeding for delivering fluids to a patent via a connected tube, wherein the connector further comprises:
a fluid receiving end that meets enteral feeding standards including ANSI/AAMI ID54:1996(R) 2005 and not mate with standards for intravenous ports and connectors including ANSI/HIMA MD70.1, ISO 594/1 and ISO 594/2 and that further includes:
at least one axially aligned channel having an axial length that is greater than a channel width for receiving the at least one axially aligned locking tab of the first fluid delivery end in an axial direction when the first fluid delivery end is inserted into the fluid receiving end of the connector; and
a locking region extending perpendicularly to the channel and configured to receive the axially aligned locking tab and to hold the first fluid delivery end when the first fluid delivery end is inserted and subsequently rotated into a locking position;

a second fluid delivery end that defines an internal conduit sized to limit a flow rate to a specified flow rate desired for a patient; and wherein the at least one channel and the at least one axially aligned locking tab are configured to enable the first fluid delivery end to be inserted axially to a final depth prior to the first fluid delivery end of the syringe or fluid delivery device being turned and locked into place.

2. The fluid delivery system of claim 1 wherein the first fluid delivery end further includes a stop flange configured to allow the first fluid delivery end and the fluid receiving end to engage and lock and to prevent connections with connectors that do not meet enteral feeding standards.

3. The fluid delivery system of claim 1 wherein the first fluid delivery end is a male connector end sized to meet standards for enteral feeding systems including ANSI/AAMI ID54:1996(R) 2005.

4. The fluid delivery system of claim 1 wherein the first fluid delivery end is a male connector end sized not to mate with devices made according to standards for I.V. delivery of medication including ANSI/HIMA MD70.1, ISO 594/1 and ISO 594/2 standards for intravenous ports and connectors.

5. The fluid delivery system of claim 1 wherein the first fluid delivery end further includes a plurality of stop flanges configured to allow the first fluid delivery end and the fluid receiving end to engage and lock and to prevent connections with connectors that do not meet enteral feeding standards.

6. The fluid delivery system of claim 1 wherein first fluid delivery end comprises a plurality of locking tabs.

7. A fluid delivery system, comprising:
a syringe for intravenous delivery of medication;
a fluid delivery device further including a female connector end sized to receive and mate with a male end of the syringe and a male connector end extending outwardly from the female connector end, the male connector end sized to meet standards for enteral feeding including ANSI/AAMI ID54:1996(R) 2005 and not mate with standards for I.V. delivery including ANSI/HIMA MD70.1, ISO 594/1 and ISO 594/2 standards for intravenous ports and connectors; and
wherein the fluid delivery device includes:
a first fluid delivery end that further includes an axially aligned locking tab for insertion into a female end of a connector having an axially aligned channel having an axial length that is greater than a channel width and configured to receive the locking tab an axial direction wherein the channel of the connector and the locking tab of the fluid delivery device are configured to enable the fluid delivery end to be inserted axially to a final depth prior to being turned and locked into place and wherein the fluid delivery device is configured to only mate with specified connector ends for enteral feeding; and
a second fluid delivery end that defines an internal conduit sized to limit a flow rate to a specified flow rate desired for a patient.

8. The fluid delivery system of claim 7 wherein the fluid delivery device is permanently attached to the syringe with a locking mechanism, an adhesive material, a bonding agent, or an application technique.

9. The fluid delivery system of claim 8 wherein the application technique comprises one of spin welding, pressure mounting or overmolding and applying.

10. The fluid delivery system of claim 8 wherein the delivery end of the fluid delivery device further includes at least one stop flange to allow the first fluid delivery end and the fluid receiving end to engage and lock and to prevent connections with connectors that do not meet enteral feeding standards.

11. A syringe system, comprising:
a chamber for temporarily holding a fluid for delivery enterally to a patient;
a male connector end fluidly connected to the chamber for delivering the fluid to a tube;
wherein the male connector end is sized to meet ANSI/AAMI ID54:1996(R) 2005 and not mate with ANSI/HIMA MD70.1 or ISO 594/1 and ISO 594/2 standards for intravenous ports and connectors; and
wherein the male connector end includes a locking tab and is configured to only mate with specified connector ends for enteral feeding and is configured for insertion into a female end of a fluid delivery device or the connector having an axially aligned channel and a perpendicularly aligned locking region and wherein the channel and locking tab are configured to enable the male connector end to be inserted axially to a final depth prior to the fluid delivery device being turned and locked into place wherein the fluid deliver device has a second fluid delivery end that defines an internal conduit sized to limit a flow rate to a specified flow rate desired for a patient.

12. The syringe system of claim 11 further comprising a connector having a connector end configured to only engage with the male connector end with the locking tab to receive fluid from the syringe.

13. The syringe system of claim 12, the connector further including a port sized to meet enteral feeding system standards including ANSI/AAMI ID54:1996(R) 2005 and coupled to the enteral feeding tube wherein the port is operable to receive and engage with the male end of the fluid delivery device.

14. The syringe system of claim 13, the connector comprising a female connector end defining an outer diameter and a wall thickness that is too large to receive a syringe for I.V. delivery of medication with a Luer connector and an inner opening with a diameter too large to matingly receive and hold a male end of the syringe.

\* \* \* \* \*